United States Patent [19]

Chiang et al.

[11] Patent Number: 5,925,807
[45] Date of Patent: Jul. 20, 1999

[54] GA4 DNA, PROTEIN AND METHOD OF USE

[75] Inventors: Hui-Hwa Chiang, Cambridge; Howard M. Goodman, Newton Centre, both of Mass.

[73] Assignee: General Hospital Corporation, Boston, Mass.

[21] Appl. No.: 08/823,986

[22] Filed: Mar. 25, 1997

Related U.S. Application Data

[63] Continuation of application No. 08/291,939, Aug. 16, 1994., abandoned

[51] Int. Cl.$^6$ .............................. A01H 5/00; A01H 5/10; C12N 5/04; C12N 15/29

[52] U.S. Cl. .......................... 800/298; 800/278; 800/286; 800/290; 536/23.6; 536/24.1; 536/24.5; 435/69.1; 435/70.1; 435/252.3; 435/254.2; 435/320.1; 435/419; 435/468

[58] Field of Search ................................. 536/23.6, 24.1, 536/24.5; 435/69.1, 70.1, 172.3, 252.3, 254.2, 320.1, 419, 468; 800/205, 230, 250, 255, 278, 286, 290, 298

[56] References Cited

U.S. PATENT DOCUMENTS

5,110,728  5/1992  Kridl et al. ............................. 435/69.1

FOREIGN PATENT DOCUMENTS

| WO93/03616 | 3/1993 | WIPO . |
| WO93/16096 | 8/1993 | WIPO . |
| WO93/18142 | 9/1993 | WIPO . |
| WO94/03606 | 2/1994 | WIPO . |
| WO94/28141 | 12/1994 | WIPO . |

OTHER PUBLICATIONS

Berry–Lowe et al., "The Nucleotide Sequence, Expression, and Evolution of One Member of a Multigene Family Encoding the Small Subunit of Ribulose–1,5–Bisphosphate Carboxylase in Soybean," *J. Mol. Appl. Genet.* 1(6):483–498 (1982).

Bevan, M., "Binary Agrobacterium vectors for plant transformation," *Nucl. Acids Res.* 12(22):8711–8721 (1984).

Britsch et al., "Molecular Cloning, Sequence Analysis, and in vitro Expression of Flavanone 3β–Hydroxylase from *Petunia hybrida*," *J. Biol. Chem.* 267(8):5380–5387 (1992).

Cashmore, A.R., "Nuclear Genes Encoding the Small Subunit of Ribulose–1,5–Bisphosphate Carboxylase," in: *Genetic Engineering of Plants, An Agricultural Perspective*, Plenium Press, New York, pp. 29–38 (1983).

Coruzzi et al., "Nucleotide Sequences of Two Pea cDNA Clones Encoding the Small Subunit of Ribulose 1,5–Bisphosphate Carboxylase and the Major Chlorophyll a/b–binding Thylakoid Polypeptide," *J. Biol. Chem.* 258(3):1399–1402 (1983).

Deikman and Fischer, "Interaction of a DNA binding factor with the 5'–flanking region of an ethylene–responsive fruit ripening gene from tomato," *EMBO J.* 7(11):3315–3320 (1988).

Dunsmuir et al., "The Major Chlorophyll a/b Binding Protein of Petunia Is Composed of Several Polypeptides Encoded by a Number of Distinct Nuclear Genes," *J. Mol. Appl. Genet.* 2(3):285–300 (1983).

Feldmann and Marks, "Agrobacterium–mediated transformation of germinating seeds of *Arabidopsis thaliana*: A non–tissue culture approach," *Mol. Gen. Genet.* 208:1–9 (1987).

Fraley et al., "Expression of bacterial genes in plant cells," *PNAS USA* 80:4803–4807 (1983).

Fujioka et al., "Qualitative and Quantitative Analyses of Gibberellins in Vegetative Shoots of Normal, dwarf–1, dwarf–2, dwarf–3, and dwarf–5 Seedlings of *Zea Mays* L.," *Plant Physiol.* 88:1367–1372 (1988).

Horsch et al., "Inheritance of Functional Foreign Genes in Plants," *Science* 233:496–498 (1984).

Ingram et al., "Internode length in Pisum," *Planta* 160:455–463 (1984).

Koornneef and van der Veen, "Induction and Analysis of Gibberellin Sensitive Mutants in *Arabidopsis thaliana* (L.) Heynh.," *Theor. Appl. Genet.* 58:257–263 (1980).

Meldgaard, M., "Expression of chalcone synthase, dihydroflavonal reductase, and flavanone–3–hydroxylase in mutants of barley deficient in anthocyanin and proanthocyanidin biosynthesis," *Theor. Appl. Genet.* 83:695–706 (1992).

Moritz and Monteiro, "Analysis of endogenous gibberellins and gibberellin metabolites from *Dalbergia dolichopetala* by gas chromatography–mass spectrometry and high–performance liquid chromatography–mass spectrometry," *Planta* 193:1–8 (1994).

Odell et al., "Identification of DNA Sequences required for activity of the cauliflower mosaic virus 35S promoter," *Nature* 313:810–812 (1985).

Phinney and Spray, "Chemical Genetics and the Gibberellin Pathway in *Zea mays* L.," In: Plant Growth Substances, P.F. Waering, Ed., Academic Press, NY, pp. 101–110 (1982).

(List continued on next page.)

*Primary Examiner*—David T. Fox
*Attorney, Agent, or Firm*—Sterne, Kessler, Goldstein & Fox, P.L.L.C.

[57] ABSTRACT

The invention relates to the DNA and protein encoded by the GA4 locus. This protein is believed to be a member of the family of enzymes involved in the biosynthesis of the gibberellin family (GA) of plant growth hormones which promote various growth and developmental processes in higher plants, such as seed germination, stem elongation, flowering and fruiting. More specifically, the protein encoded by the GA4 locus is an hydroxylase. The invention also relates to vectors containing the DNA and the expression of the protein encoded by the DNA of the invention in a host cell. Additional aspects of the invention are drawn to host cells transformed with the DNA or antisense sequence of the invention, the use of such host cells for the maintenance, or expression or inhibition of expression of the DNA of the invention and to transgenic plants containing DNA of the invention. Finally, the invention also relates to the use of the protein encoded by the GA4 locus to alter aspects of plant growth.

17 Claims, 9 Drawing Sheets

OTHER PUBLICATIONS

Ross et al., "Internode length in Pisum. Estimation of GA$_1$ levels in genotypes Le, le and le$^d$," *Physiol. Plant.* 76:173–176 (1989).

Talon et al., "Endogenous gibberellins in *Arabidopsis thaliana* and possible steps blocked in the biosynthetic pathways of the semidwarf ga4 and ga5 mutants," *PNAS USA* 87:7983–7987 (1990).

van der Krol et al., "Antisense genes in plants: an overview," *Gene* 72:45–50 (1988).

van der Krol et al., "Inhibition of flower pigmentation by antisense CHS genes: promoter and minimal sequence requirements for the antisense effect," *Plant Mol. Biol.* 14:457–466 (1990).

Walden et al., "T–DNA as a gene tag," *Plant J.* 1(3):281–288 (1991).

Zhang et al., "Expression of Antisense or Sense RNA of an Ankyrin Repeat–Containing Gene Blocks Chloroplast Differentiation in Arabidopsis," *Plant Cell* 4:1575–1588 (1992).

Britsch et al., "Molecular Characterization of Flavonone 3Beta–hydroxylases, Consesus Sequence, Comparison with Related Enzymes and the Role of Conserved Histidine Residues," *Eur. J. Biochem.* 217:745–754 (Oct. 1993).

Chiang et al., "Isolation of the Arabidopsis GA4 Locus," *The Plant Cell* 7(2): 195–201 (1995).

Dehio et al., "Phenotype and Hormonal Status of Transgenic Tobacco Plants Overexpressing the rolA Gene of *Agrobacterium rhizogenes* T–DNA," *Plant Molecular Biology* 23: 1199–1210 (Dec. 1993).

Lange et al., "Separation and Characterisation of Three 2–Oxoglutarate–dependent Dioxygenases from *Curcurbita maxima* L. Endosperm Involved in Gibberellin Biosynthesis," *Planta* 195(1): 98–107 (Apr. 1994).

Nilsson et al., "Hormonal Characterization of Transgenic Tobacco Plants Expressing the rolC Gene of *Agrobacterium rhizogenes* TL–DNA," *Plant Physiol.* 102: 363–371 (Jun. 1993).

Schmulling et al., "Hormonal Content and Sensitivity of Transgenic Tobacco and Potato Plants Expressing Single rol Genes of *Agrobacterium rhizogenes* T–DNA," *The Plant Journal* 3(3): 371–382 (Mar. 1993).

Smith et al., "Partial Purification and Characterization of the Gibberellin A20 3Beta–hydroxylase from seeds of *Phaseolus vulgaris*," *Plant Physiol.* 94(3): 1390–1401 (1990).

Spray et al., "Internode Length in *Zea mays* (L). The Dwarf–1 Mutation Controls the 3 Beta–hydroxylation of Gibberellin A20 to Gibberellin A1," *Planta* 160: 464–468 (1984).

Smith et al. 1988. Nature 334:724–726.

Napoli et al. 1990. The Plant Cell 2:279–289.

```
TCGAGGTCGACGGTATCGATAAGCTTGATATCGAATTCGGATAAGAAAAAAAACACAAAC
ATCTATCAAATTTACAAAGTTTTAAAACTAATTAAAAAAGAGCAAG
```

```
  1  ATGCCTGCTATGTTAACAGATGTGTTTAGAGGCCATCCCATTCACCTCCCACACTCTCAC   60
  1   M  P  A  M  L  T  D  V  F  R  G  H  P  I  H  L  P  H  S  H   20

61  ATACCTGACTTCACATCTCTCCGGGAGCTCCCGGATTCTTACAAGTGGACCCCTAAAGAC  120
 21   I  P  D  F  T  S  L  R  E  L  P  D  S  Y  K  W  T  P  K  D   60

121  GATCTCCTCTTCTCCGCTGCTCCTTCTCCTCCGGCCACCGGTGAAAACATCCCTCTCATC  180
 41   D  L  L  F  S  A  A  P  S  P  P  A  T  G  E  N  I  P  L  I   60

181  GACCTCGACCACCCGGACGCGACTAACCAAATCGGTCATGCATGTAGAACTTGGGGTGCC  240
 61   D  L  D  H  P  D  A  T  N  Q  I  G  H  A  C  R  T  W  G  A   80

241  TTCCAAATCTCAAACCACGGCGTGCCTTTGGGACTTCTCCAAGACATTGAGTTTCTCACC  300
 81   F  Q  I  S  N  H  G  V  P  L  G  L  L  Q  D  I  E  F  L  T  100

301  GGTAGTCTCTTCGGCTACCTGTCCAACGCAAGCTTAAGTCTGCTCGGTCGGAGACAGGT   360
101   G  S  L  F  G  L  P  V  Q  R  K  L  K  S  A  R  S  E  T  G   120

361  GTGTCCGGCTACGCGTCGCTCGTATCGCATCTTTCTTCAATAAGCAAATGTGGTCCGAAG  420
121   V  S  G  Y  A  S  L  V  S  H  L  S  S  I  S  K  C  G  P  K   140

421  GTTTCACCATCACTGGCTCGCCTCTCAACGATTTCCGTAAACTTTGGCCCCAACATCACC  480
141   V  S  P  S  L  A  R  L  S  T  I  S  V  N  F  G  P  N  I  T   160

481  TCAACTACTGCGATATCGTATGAAGAGTACGAGGAACATATGAAAAAGTTGGCATCGAAA  540
161   S  T  T  A  I  S  Y  E  E  Y  E  E  H  M  K  K  L  A  S  K   180

541  TTGATGTGGTTAGCACTAAATTCACTTGGGGTCAGCGAAGAAGACATTGAATGGGCCAGT  600
181   L  M  W  L  A  L  N  S  L  G  V  S  E  E  D  I  E  W  A  S   200

601  CTCAGTTCAGATTTAAACTGGGCCCAAGCTGCTCTCCAGCTAAATCACTACCCGGTTTGT  660
201   L  S  S  D  L  N  W  A  Q  A  A  L  Q  L  N  H  Y  P  V  C   220

661  CCTGAACCGGACCGAGCCATGGGTCTAGCAGCTCATACCGACTCCACCCTCCTAACCATT  720
221   P  E  P  D  R  A  M  G  L  A  A  H  T  D  S  T  L  L  T  I   240
```

FIG.4A

```
721   CTGTACCAGAACAATACCGCCGGTCTACAAGTATTTCGCGATGATCTTGGTTGGGTCACC   780
241    L  Y  Q  N  N  T  A  G  L  Q  V  F  R  D  D  L  G  W  V  T   260

781   GTGCCACCGTTTCCTGGCTCGCTCGTGGTTAACGTTGGTGACCTCTTCCACATCCTATCC   840
261    V  P  P  F  P  G  S  L  V  V  N  V  G  D  L  F  H  I  L  S   280

841   AATGGATTGTTTAAAAGCGTGTTGCACCGCGCTCGGGTTAACCAAACCAGAGCCCGGTTA   900
281    N  G  L  F  K  S  V  L  H  R  A  R  V  N  Q  T  R  A  R  L   300

901   TCTGTAGCATTCCTTTGGGGTCCGCAATCTGATATCAAGATATCACCTGTACCGAAGCTG   960
301    S  V  A  F  L  W  G  P  Q  S  D  I  K  I  S  P  V  P  K  L   320

961   GTTAGTCCCGTTGAATCGCCTCTATACCAATCGGTGACATGGAAAGAGTATCTTCGAACA  1020
321    V  S  P  V  E  S  P  L  Y  Q  S  V  T  W  K  E  Y  L  R  T   340

1021  AAAGCAACTCACTTCAACAAAGCTCTTTCAATGATTAGAAATCACAGAGAAGAATGA    1077
341    K  A  T  H  F  N  K  A  L  S  M  I  R  N  H  R  E  E  *     359

TTAGATAATAATAGTTGTGATCTACTAGTTAGTTTGATTAATAAATTGTTGTAAATGATT
      TCAGCAATATGATTTGTTTGTCCTCAA
```

FIG.4B

| | | | | |
|---|---|---|---|---|
| 1 | tcgaggtcga | cggtatcgat | aagcttgata | tcgaattcgg | ataagaaaaa |
| 51 | aaacacaaac | atctatcaaa | tttacaaagt | tttaaaacta | attaaaaaag |
| 101 | agcaagatgc | ctgctatgtt | aacagatgtg | tttagaggcc | atcccattca |
| 151 | cctcccacac | tctcacatac | ctgacttcac | atctctccgg | gagctcccgg |
| 201 | attcttacaa | gtggacccct | aaagacgatc | tcctcttctc | cgctgctcct |
| 251 | tctcctccgg | ccaccggtga | aaacatccct | ctcatcgacc | tcgaccaccc |
| 301 | ggacgcgact | aaccaaatcg | gtcatgcatg | tagaacttgg | ggtgccttcc |
| 351 | aaatctcaaa | ccacggcgtg | cctttgggac | ttctccaaga | cattgagttt |
| 401 | ctcaccggta | gtctcttcgg | gctacctgtc | caacgcaagc | ttaagtctgc |
| 451 | tcggtcggag | acaggtgtgt | ccggctacgc | gtcgctcgta | tcgcatcttt |
| 501 | cttcaataag | caaatgtggt | ccgaaggttt | caccatcact | ggctcgcctc |
| 551 | tcaacgattt | ccgtaaactt | tggccccaac | atcacctcaa | ctactggtat |
| 601 | atctttata | cactcgatcc | tatatacttg | tacttgtgtt | tattagacct |
| 651 | ttttctacat | taacaaaaaa | catatacata | aggacacaat | gtttacattt |
| 701 | aaggtagaac | atccacaaac | gttggacgcc | ctataggtag | taacaagggg |
| 751 | catagataac | agaagcaacc | gaaatttgcc | ttgtcctcgg | agtttagtgg |
| 801 | atttaagagt | taagtgcata | atgaaatcta | gtgtagtagt | ggacccaact |
| 851 | caaagatttt | gaagatatgt | attctttaa | tcttatcgga | gaaaacaaaa |
| 901 | caaaaaaaca | acaacttgct | tttctatttt | attaaaggt | cgtacaaata |
| 951 | tttaatgtat | gtatatgcaa | attgtgtcta | aatctcatct | gtactaatta |
| 1001 | gatgaataca | attcgttttt | aattaacagc | gatatcgtat | gaagagtacg |

FIG.5A

```
1051  aggaacatat gaaaaagttg gcatcgaaat tgatgtggtt agcactaaat 1101  tcacttgggg tcagcgaaga agacattgaa tgggccagtc tcagttcaga 1151  tttaaactgg gcccaagctg ctctccagct aaatcactac ccggtttgtc 1201  ctgaaccgga ccgagccatg ggtctagcag ctcataccga ctccaccctc 1251  ctgaccattc tgtaccagaa caataccgcc ggtctacaag tatttcgcga 1301  tgatcttggt tgggtcaccg tgccaccgtt tcctggctcg ctcgtggtta 1351  acgttggtga cctcttccac atcctatcca atggattgtt taaaagcgtg 1401  ttgcaccgcg ctcgggttaa ccaaaccaga gcccggttat ctgtagcatt 1451  cctttggggt ccgcaatctg atatcaagat atcacctgta ccgaagctgg 1501  ttagtcccgt tgaatcgcct ctataccaat cggtgacatg gaaagagtat 1551  cttcgaacaa aagcaactca cttcaacaaa gctctttcaa tgattagaaa
                                              *
1601  tcacagagaa gaatgattag ataataatag ttgtgatcta ctagttagtt 1651  tgattaataa attgttgtaa atgatttcag caatatgatt tgtttgtcct 1701  caa
```

▼ ATG INITIATION CODON
* TGA STOP CODON
— INTRON

FIG.5B

```
         1                                                         50
GA4   MPAMLTDVFR GHPIHLPHSH IPDFTSLREL PDSYKWTPKD DLLFSAAPSP
F3H   ........MA PVSNETFLPT EAWGEATLRP SFVRDEDERP KVAHDRFSDA

GA4   PATGENIPLI DLDHPDATNQ IGHACRTWGA FQISNHGVPL GLLQDIEFLT
F3H   VPLISLHGID GARRAQIRDR VAAACEDWGI FQVIDHGVDA DLIADMTRLA

GA4   GSLFGLPVQR KLKSARSETG VSGYASLVSH LSSISKCGPK VSPSLARLST
F3H   REFFALPAED KLRYDMSGGK KGGF.IVSSH LQGEAVQDWR EIVTYFSYPV

GA4   ISVNFG..PN ITSTTAISYE EYEEHMKKLA SKLMWLALNS LGVSEEDIEW
F3H   KARDYGRWPE KPAGWCAVVE RYSERLMGLS CNLMGVLSEA MGLETEALAK

GA4   ASLSSDLNWA QAALQLNHYP VCPEPDRAMG LAAHTDSTLL TILYQNNTAG
F3H   ACVDMD.... .QKVVVNFYP RCPQPDLTLG LKRHTDPGTI TLLLQDLVGG

GA4   LQVFRD.DLG WVTVPPFPGS LVVNVGDLFH ILSNGLFKSV LHRARVNQTR
F3H   LQATRDGGKN WITVQPISGA FVVNLGDHGH FMSNGRFKNA DHQAVVNGES

GA4   ARLSVAFLWG PQSDIKISPV PKLVSPVESP LYQSVTWKEY LRTKATHFNK
F3H   SRLSIATFQN PAPDARVWPL A.VREGEEPI LEEPITFTEM YRRKMER.DL

GA4   ALSMIRNHRE E......... .......... .......... ...
F3H   DLAKRKKQAK DQLMQQQLQL QQQQAVAAAP MPTATKPLNE ILA
```

FIG.6

+ - + - GA3
24 24 8 8 hrs

GA4 DNA, PROTEIN AND METHOD OF USE

This application is a continuation of application No. 08/291,939, filed Aug. 16, 1994, now abandoned.

This invention was made with government support; the government may have certain rights in this invention.

FIELD OF THE INVENTION

The invention relates to the field of molecular biology and plant growth hormones, and especially to gibberellins.

BACKGROUND OF THE INVENTION

Gibberellins are a large family of tetracyclic triterpenoid plant growth hormones which promote various growth and developmental processes in higher plants, such as seed germination, stem elongation, flowering and fruiting (Stowe, B. B. et al., Annu. Rev. Plant Physiol. 8:181–216 (1957)). A number of GA responsive dwarf mutants have been isolated from various plant species, such as maize, pea, and Arabidopsis (Phinney, B.O. et al., "Chemical Genetics and the Gibberellin Pathway" in Zea mays L. in *Plant Growth Substance, ed.,* P. F. Waering, N.Y.: Academic (1982) pp. 101–110; Ingram, T. J. et al., Planta 160:455–463 (1984); Koornneef, M., Arabidopsis Inf. Serv. 15:17–20. (1978)). The dwarf mutants of maize (dwarf-1, dwarf-2, dwarf-3, dwarf-5) have been used to characterize the maize GA biosynthesis pathway by determining specific steps leading to biologically important metabolites (Phinney, B. O. et al., "Chemical Genetics and the Gibberellin Pathway" in Zea mays L. in *Plant Growth Substance, ed.,* P. F. Waering, N.Y.: Academic (1982) pp. 101–110; Fujioka, S. et al., *Plant Physiol.* 88:1367–1372 (1988)). Similar studies have been done with the dwarf mutants from pea (Pisum sativum L.) (Ingram, T. J. et al., Planta 160:455–463 (1984)). GA deficient mutants have also been isolated from Arabidopsis (ga1, ga2, ga3, ga4, ga5) (Koornneef, M., et al., Theor. Appl. Genet. 58:257–263 (1980)). The Arabidopsis ga4 mutant, induced by ethyl methanesulfonate (EMS) mutagenesis, is a germinating, GA responsive, semidwarf whose phenotype can be restored to wild type by repeated application of exogenous GA (Koornneef, M. et al., Theor. Appl. Genet. 58:257–263 (1980)).

In Arabidopsis, the ga4 mutant allele blocks the conversion of 3-β-hydroxy GAs, reducing the endogenous levels of $GA_1$, $GA_8$ and $GA_4$ and increasing the endogenous levels of $GA_{19}$, $GA_{20}$ and $GA_9$ (Talon, M. et al., *Proc. Natl. Acad. Sci. USA* 87:7983–7987 (1990)). The reduced levels of the 3-β-hydroxy GAs is the cause of the semidwarf phenotype of the ga4 mutant. It has been suggested that the pea le mutant also encodes an altered form of 3-β-hydroxylase (Ross, J. J. et al., *Physiol. Plant.* 76:173–176 (1989)).

SUMMARY OF THE INVENTION

The invention is first directed to GA4 DNA and the protein encoded by the GA4 DNA.

The invention is further directed to GA4 antisense DNA, and to the GA4 antisense RNA transcribed from it.

The invention is further directed to vectors containing GA4 encoding DNA and to the expression of GA4 protein encoded by the GA4 DNA in a host cell.

The invention is further directed to vectors containing GA4 antisense DNA and to the expression of GA4 antisense RNA by the GA4 antisense DNA in a host cell.

The invention is further directed to host cells transformed with the GA4 encoding DNA of the invention, and to the use of such host cells for the maintenance of the GA4 DNA or expression of the GA4 protein of the invention.

The invention is further directed to host cells transformed with the GA4 antisense DNA of the invention, and to the use of such host cells for the maintenance of the GA4 DNA or inhibition of expression of the GA4 protein of the invention.

The invention is further directed to transgenic plants containing the GA4 encoding or GA4 antisense DNA of the invention.

The invention is further directed to a method for altering plant growth, using the GA4 encoding or GA4 antisense DNA of the invention.

The invention is further directed to a method for altering plant growth, using the recombinantly made GA4 protein of the invention.

BRIEF DESCRIPTION OF THE DRAWINGS

FIGS. 4A–4B: Nucleotide [SEQ ID No. 1] and deduced amino acid sequence [SEQ ID No. 2] of the GA4 cDNA clone. The position of the intron as deduced from a comparison of cDNA and genomic sequences is indicated with a down arrowhead ▼ above the relevant line. The EMS-induced mutation at nucleotide 725 is indicated with a star (*) above that position. The underlined area indicates the sequence of the PCR labeled probe used for RNA gel blot analysis.

FIGS. 5A–5B: Nucleotide sequence [SEQ ID No. 3] of GA4 genomic DNA. The intron is underlined. The ATG initiation codon is indicated with a down arrowhead ▼ above and in front of the "A." The TGA stop codon is indicated with a star (*) above and after the "A.".

FIG. 6: Amino acid sequence comparison of GA4 and barley flavanone-3-hydroxylase (F3H) [SEQ ID No. 4]. Identical residues are shown in bold type.

DEFINITIONS

Figure 1:
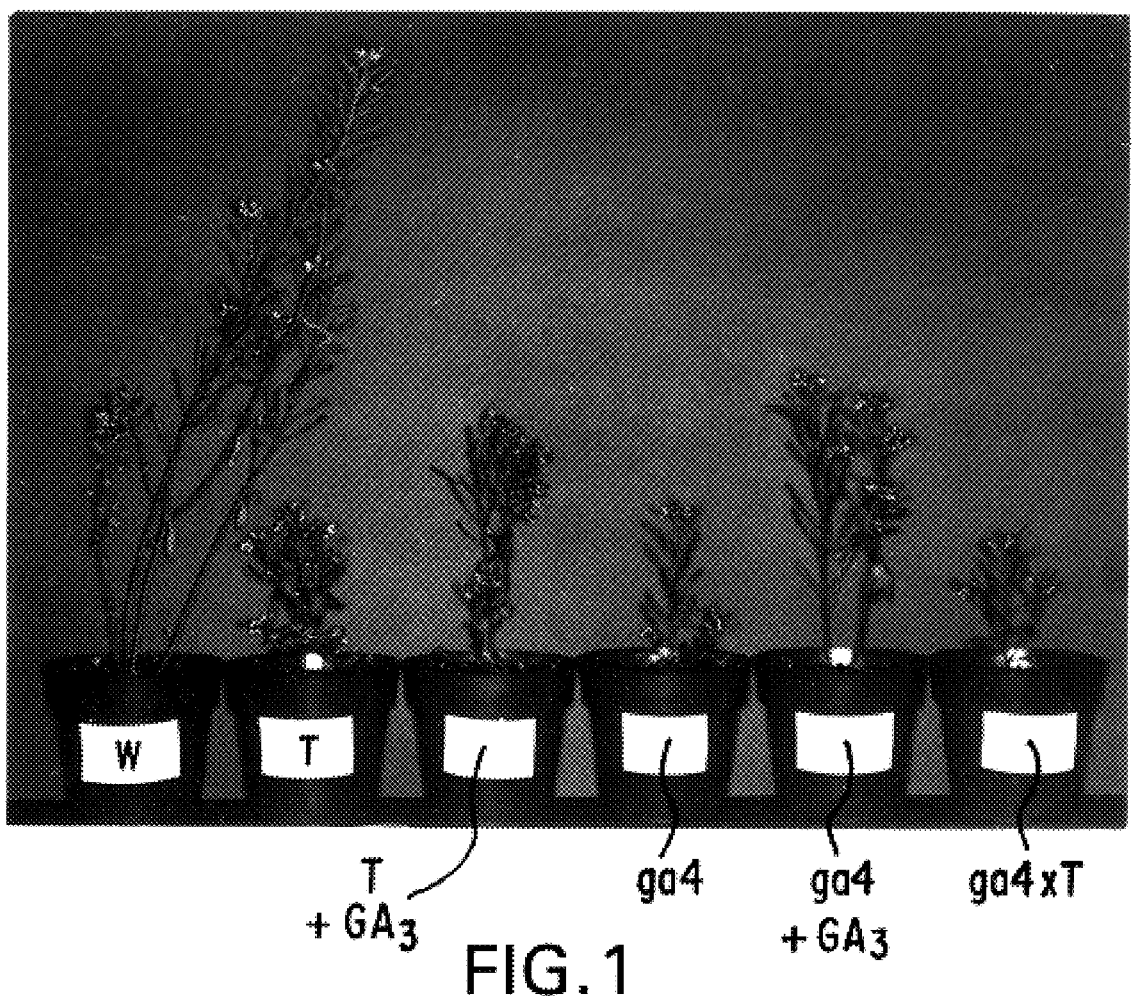
FIG. 1: T-DNA tagged mutant (T) is an allele of the ga4 locus. Both the T-DNA tagged allele, ga4-2 (T) and the EMS-induced allele, ga4-1 (ga4), respond to $GA_3$ treatment with shoot elongation (T+$GA_3$ and ga4+$GA_3$, respectively). W, canonical wild type, Landsberg er; T, ga4-2; and ga4, ga4-1.

Italicized, uppercase names, such as "GA4, " refer to the wild type gene while italicized, lower case names, such as "ga4," refer to the mutant gene.

Uppercase names, such as "GA4," refer to the protein, DNA or RNA encoded by the GA4 gene, while lowercase names, such as "ga4," refer to the protein DNA or RNA encoded by the mutant ga4 gene. "GA$_n$" (with a number subscripted), refers to the "gibberellin A$_n$" compound. The chemical structures of some of the gibberellin A$_n$'s are presented in Moritz, T. et al., Planta 193:1–8 (1994).

Plant should be understood as referring to a multicellular differentiated organism capable of photosynthesis including angiosperms (monocots and dicots) and gymnosperms.

Plant cell should be understood as referring to the structural and physiological unit of plants. The term "plant cell" refers to any cell which is either part of or derived from a plant. Some examples of cells encompassed by the present invention include differentiated cells that are part of a living plant; differentiated cells in culture; undifferentiated cells in culture; the cells of undifferentiated tissue such as callus or tumors.

Plant cell progeny should be understood as referring to any cell or tissue derived from plant cells including callus; plant parts such as stems, roots, fruits, leaves or flowers; plants; plant seed; pollen; and plant embryos.

Propagules should be understood as referring to any plant material capable of being sexually or asexually propagated, or being propagated in vivo or in vitro. Such propagules preferably consist of the protoplasts, cells, calli, tissues, embryos or seeds of the regenerated plants.

Transgenic plant should be understood as referring to a plant having stably incorporated exogenous DNA in its genetic material. The term also includes exogenous DNA which may be introduced into a cell or protoplast in various forms, including, for example, naked DNA in circular, linear or supercoiled form, DNA contained in nucleosomes or chromosomes or nuclei or parts thereof, DNA complexed or associated with other molecules, DNA enclosed in liposomes, spheroplasts, cells or protoplasts.

A fragment of a molecule should be understood as referring to a shortened sequence of an amino acid or nucleotide genetic sequence that retains some desired chemical or biological property of the full-length sequence such that use of the full-length sequence is not necessary to achieve the desired purpose.

A mutation should be understood as referring to a detectable change in the genetic material which may be transmitted to daughter cells and possibly even to succeeding generations giving rise to mutant cells or mutant organisms. If the descendants of a mutant cell give rise only to somatic cells in multicellular organisms, a mutant spot or area of cells arises. Mutations in the germ line of sexually reproducing organisms may be transmitted by the gametes to the next generation resulting in an individual with the new mutant condition in both its somatic and germ cells. A mutation may be any (or a combination of) detectable, unnatural change affecting the chemical or physical constitution, mutability, replication, phenotypic function, or recombination of one or more deoxyribonucleotides; nucleotides may be added, deleted, substituted for, inverted, or transposed to new positions with and without inversion. Mutations may occur spontaneously and can be induced experimentally by application of mutagens. A mutant variation of a nucleic acid molecule results from a mutation. A mutant polypeptide may result from a mutant nucleic acid molecule.

A species should be understood as referring to a group of actually or potentially interbreeding natural populations. A species variation within a nucleic acid molecule or protein is a change in the nucleic acid or amino acid sequence that occurs among species and may be determined by DNA sequencing of the molecule in question.

A preparation that is substantially free of other *A. thaliana* DNA (or protein) should be understood as referring to a preparation wherein the only *A. thaliana* DNA (or protein) is that of the recited *A. thaliana* DNA (or protein). Though proteins may be present in the sample which are homologous to other *A. thaliana* proteins, the sample is still said to be substantially free of such other *A. thaliana* DNA (or protein) as long as the homologous proteins contained in the sample are not expressed from genes obtained from A. thaliana.

A DNA construct should be understood as referring to a recombinant, man-made DNA, linear or circular.

T-DNA (transferred DNA) should be understood as referring to a segment or fragment of Ti (tumor-inducing) plasmid DNA which integrates into the plant nuclear DNA.

Stringent hybridization conditions should be understood to be those conditions normally used by one of skill in the art to establish at least a 90% homology between complementary pieces of DNA or DNA and RNA. Lesser homologies, such as at least 70% homology or preferably at least 80% may also be desired and obtained by varying the hybridization conditions.

There are only three requirements for hybridization to a denatured strand of DNA to occur. (1) There must be complementary single strands in the sample. (2) The ionic strength of the solution of single-stranded DNA must be fairly high so that the bases can approach one another; operationally, this means greater than 0.2M. (3) The DNA concentration must be high enough for intermolecular collisions to occur at a reasonable frequency. The third condition only affects the rate, not whether renaturation/hybridization will occur.

Conditions routinely used by those of skill in the art are set out in readily available procedure texts, e.g., *Current Protocol in Molecular Biology*, Vol. 1, Chap. 2.10, John Wiley & Sons, Publishers (1994) or Sambrook et al., *Molecular Cloning*, Cold Spring Harbor (1989), incorporated herein by reference. As would be known by one of skill in the art, the ultimate hybridization stringency reflects both the actual hybridization conditions as well as the washing conditions following the hybridization, and one of skill in the art would know the appropriate manner in which to change these conditions to obtain a desired result.

For example, a prehybridization solution should contain sufficient salt and nonspecific DNA to allow for hybridization to non-specific sites on the solid matrix, at the desired temperature and in the desired prehybridization time. For example, for stringent hybridization, such prehybridization solution could contain 6× single strength citrate (SSC) (1×SC is 0.15 M NaCl, 0.015 M Na citrate; pH 7.0), 5×Denhlardt's solution, 0.05% sodium pyrophosphate and 100 μg per ml of herring sperm DNA. An appropriate stringent hybridization mixture might then contain 6×SSC, 1×Denhardt's solution, 100 μg per ml of yeast tRNA and 0.05% sodium pyrophosphate.

Alternative conditions for DNA-DNA analysis could entail the following:

1) prehybridization at room temperature and hybridization at 68° C.;
2) washing with 0.2×SSC/0.1% SDS at room temperature;
3) as desired, additional washes at 0.2×SSC/0. 1% SDS at 42° C. (moderate-stringency wash); or 4) as desired, additional washes at 0.1×SSC/0.% SDS at 68° C. (high stringency).

Known hybridization mixtures, e.g., that of Church and Gilbert, *Proc. Natl. Acad. Sci. USA* 81:1991–1995 (1984), comprising the following composition may also be used: 1% crystalline grade bovine serum albumin/1 mM EDTA/0.5M NaHPO$_4$, pH 7.2/7% SDS. Additional, alternative but similar reaction conditions can also be found in Sambrook et al., *Molecular Cloning*, Cold Spring Harbor (1989). Formamide may also be included in prehybridizationi/lhybridization solutions as desired.

It should be understood that these conditions are not meant to be definitive or limiting and may be adjusted as required by those of ordinary skill in the art to accomplish the desired objective.

A vector should be understood to be a DNA element used as a vehicle for cloning or expressing a desired sequence, such as a gene of the invention, in a host.

A host or host cell should be understood to be a cell in which a sequence encoding a GA4 DNA of the invention is incorporated and expressed. A GA4 gene of the invention or the antisense of the gene may be introduced into a host cell as part of a vector by transformation. Both the sense and the antisense DNA sequences are present in the same host cell since DNA is double stranded. The direction of transcription, however, as directed by an operably linked promoter as designed by the artisan, dictates which of the two strands is ultimately copied into RNA.

DETAILED DESCRIPTION

The process for genetically engineering GA4 protein sequences, according to the invention, is facilitated through the cloning of genetic sequences that are capable of encoding the GA4 protein and through the expression of such genetic sequences. As used herein, the term "genetic sequences" is intended to refer to a nucleic acid molecule (preferably DNA). Genetic sequences that are capable of encoding GA4 protein can be derived from a variety of sources. These sources include genomic DNA, cDNA, synthetic DNA, and combinations thereof. The preferred source of the ga4 genomic DNA is a plant genomic library and most preferably an *Arabidopsis thaliana* genomic library. A more preferred source of the GA4 cDNA is a plant cDNA library and most preferably an *Arabidopsis thaliana* cDNA library made from silique mRNA, although the message is ubiquitously expressed in the root, leaf and flower of plants.

The recombinant GA4 cDNA of the invention will not include naturally occurring introns if the cDNA was made using mature GA4 mRNA as a template. Genomic DNA may or may not include naturally occurring introns. Moreover, such genomic DNA may be obtained in association with the homologous (isolated from the same source; native) 5' promoter region of the GA4 gene sequences and/or with the homologous 3' transcriptional termination region. Further, such genomic DNA may be obtained in association with the genetic sequences which provide the homologous 5' non-translated region of the GA4 mRNA and/or with the genetic sequences which provide the homologous 3' non-translated region.

In plants, the GA4 sequences of the invention can be identified using T-DNA insertion mutants. In a T-DNA insertion mutant, the mutant phenotype is a result of the T-DNA insertion. A genomic library from such a mutant can be screening for the T-DNA element, and the flanking sequence analyzed to determine the native sequence that was disrupted by the T-DNA and thus led to the phenotype of the mutant plant.

The T-DNA generally carries a resistance selection marker, such as that for kanamycin, that is used to identify outcrosses that retain the T-DNA. This confirms co-segregation of the mutant phenotype and the T-DNA insert. Having identified a T-DNA mutant with the T-DNA inserted at the site of the GA4 gene, the T-DNA then becomes a tag with which the ga4 mutant gene (flanking both sides of the T-DNA insertion) can be isolated and used to identify other GA4 genes in libraries from nonmutants of the same species or in libraries made from other species, Walden et al., *Plant J.*, 1: 281–288 (1991). Additional tests, such as DNA gel blot analysis can then be used to confirm that the T-DNA insert is present in the gene of interest, here the ga4 gene.

As exemplified herein from *Arabidopsis thaliana*, the Arabidopsis ga4 mutant plant used to identify the GA4 (wild type) and ga4 (mutant) genetic sequences of the invention is deficient in an enzyme of the gibberellin biosynthetic pathway called 3 1-β-hydroxylase. Accordingly, it is believed that the site of T-DNA insertion in the ga4 mutants of the invention is in the GA4 gene that encodes the 3-β-hydroxylase of the gibberellin biosynthetic pathway.

The genomic sequence of GA4, including introns, is shown in FIGS. 5A–5B [SEQ ID No. 3]. The cDNA sequence of GA4 is shown in FIGS. 4A–4B [SEQ ID No. 1] as is the sequence of the GA4 protein encoded by the sequence [SEQ ID No. 2]. A single base mutation of G to A occurs at base 725 in a ga4 mutant that was produced by chemical (EMS) mutation, as described in the Examples. This results in an amino acid change from cystein to tyrosine.

Due to the degeneracy of nucleotide coding sequences, and to the fact that the DNA code is known, all other DNA sequences which encode the same amino acid sequence as depicted in FIGS. 4A–4B [SEQ ID No. 2] can be determined and used in the practice of the present invention. Additionally, those sequences that hybridize to sequence ID Nos. 1 or 3 under stringent conditions are also useful in the practice of the present invention.

A DNA sequence encoding GA4 protein or GA4 antisense RNA can be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. In one embodiment of the invention, expression vectors are provided that are capable of expressing GA4 in RNA or antisense RNA. Vectors for propagating a given sequence in a variety of host systems are well known and can readily be altered by one of skill in the art such that the vector will contain DNA or RNA encoding the desired genetic sequence and will be propagated in a desired host. Such vectors include plasmids and viruses and such hosts include eukaryotic organisms and cells, for example plant, yeast, insect, plant, mouse or human cells, and prokaryotic organisms, for example *E. coli* and *B. subtilus*. Shuttle vectors in which the desired genetic sequence is "maintained" in an available form before being extracted and transformed into a second host for expression are also useful DNA constructs envisioned as carrying the DNA of the invention.

A nucleic acid molecule, such as DNA, is said to be "capable of expressing" a polypeptide or antisense sequence if it contains a nucleotide sequence that encodes such polypeptide or antisense sequence and transcriptional and, if necessary, translational regulatory information operably linked to the nucleotide sequences that encode the polypeptide or antisense sequence.

Two DNA sequences (such as a promoter region sequence and the ga4 or GA4 gene encoding or antisense sequence) are said to be operably linked if the nature of the linkage between the two DNA sequences does not (1) result in the introduction of a frame-shift mutation, (2) interfere with the ability of the promoter region sequence to direct the transcription of the desired sequence, or (3) interfere with the ability of the desired sequence to be transcribed by the promoter region sequence. Thus, a promoter region would be operably linked to a desired DNA sequence if the promoter were capable of effecting transcription of that DNA sequence.

Preferred prokaryotic hosts include bacteria such as *E. coli*, Bacillus, Streptornyces, Pselzdomonas, Salnionella, Serratia, etc. The most preferred prokaryotic host is *E. coli*. The procaryotic host must be compatible with the replicon and control sequences in the expression plasmid.

Preferred eukaryotic hosts include plants, yeast, fungi, insect cells, mammalian cells. These hosts can be utilized for production of the desired genetic sequence, or GA4 or ga4 protein, in conventional methods, such as by growth in shake flasks, fermentors, tissue culture plates or bottles. Alternatively, multicellular organisms such as a plant might be used.

In one embodiment, a vector is employed that is capable of integrating the desired gene sequences into the host cell chromosome. Cells that have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection.

In another embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

DNA encoding the desired protein is preferably operably linked to a promoter region, a transcription initiation site, and a transcription termination sequence, functional in plants. Any of a number of promoters which direct transcription in a plant cell is suitable. The promoter can be either constitutive or inducible. Some examples of promoters functional in plants include the nopaline synthase promoter and other promoters derived from native Ti plasmids, viral prom-oters including the 35S and 19S RNA promoters of cauliflower mosaic virus (Odell et al., *Nature* 313:810–812 (1985)), and numerous plant promoters.

Alternative promoters that may be used include nos, ocs, and CaMV promoters. Overproducing plant promoters may also be used. Such promoters, operably linked to the GA4 gene, should increase the expression of the GA4 protein. Overproducing plant promoters that may be used in this invention include the promoter of the small subunit (ss) of ribulose-1,5-biphosphate carboxylase from soybean (Berry-Lowe et al., *J. Molecular and App. Gen.* 1:483 498 (1982), and the promoter of the chlorophyll a/b binding protein. These two promoters are known to be light-induced in eukaryotic plant cells (see, for example, *Genetic Engineering of Plants, an Agricultural Perspective*, A. Cashmore, Plenum, N.Y. 1983, pages 29–38; Corruzi, G. et al., *J. of Biol. Chem.* 258:1399 (1983); and Dunsmuir, P. et al., J. of *Mol. and Applied Genet.* 2:285 (1983)).

Genetic sequences comprising the desired gene or antisense sequence operably linked to a plant promoter may be joined to secretion signal sequences and the construct ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in trans-formed host cells, typically antibiotic resistance genes.

General methods for selecting transgenic plant cells containing a selectable marker are well known and taught, for example, by Herrera-Estrella, L. and Simpson, J. (1988) "Foreign Gene Expression in Plants" in *Plant Molecular Biology, A Practical Approach*, Ed. C. H. Shaw, IRL Press, Oxford, England, pp. 131–160.

In another embodiment, the present invention relates to a transformed plant cell comprising exogenous copies of DNA (that is, copies that originated outside of the plant) encoding a GA4 gene expressible in the plant cell wherein said plant cell is free of other foreign marker genes (preferably, other foreign selectable marker genes); a plant regenerated from the plant cell; progeny or a propagule of the plant; and seed produced by the progeny.

Plant transformation techniques are well known in the art and include direct transformation (which includes, but is not limited to: microinjection (Crossway, *Mol. Gen. Genetics* 202:179–185 (1985)), polyethylene glycol transformation (Krens et al., *Nature* 296:72–74 (1982)), high velocity ballistic penetration (Klein et al., *Nature* 327:70–73 (1987)), fusion of protoplasts with other entities, either minicells, cells, lysosomes, or other fusible lipid-surfaced bodies (Fraley et al., *Proc. Natl. Acad. Sci. USA* 79:1859–1863 (1982)), electroporation (Fromm et al., *Proc. Natl. Acad. Sci. USA* 82:5824 (1985)) and techniques set forth in U.S. Pat. No. 5,231,019)) and *Agrobacterium tumefaciens* mediated transformation as described herein and in (Hoekema et al., *Nature* 303:179 (1983), de Framond et al., *Bio/technology* 1:262 (1983), Fraley et al. WO84/02913, WO84/02919 and WO84/02920, Zambryski et al. EP 116,718, Jordan et al., *Plant Cell Reports* 7:281–284 (1988), Leple et al. *Plant Cell Reports* 11:137 141 (1992), Stomp et al., *Plant Physiol.* 92:1226–1232 (1990), and Knauf et al., Plasmid 8:45–54 (1982)). Another method of transformation is the leaf disc transformation technique as described by Horsch et al. Science 227:1229–1230 (1985).

The transformation techniques can utilize a DNA encoding the GA4 amino acid sequence of FIGS. 4A–4B [SEQ ID No. 2], including the GA4 DNA sequence of FIGS. 4A–4B SEQ ID No. 1, the GA4 genomic sequence of FIGS. 5A–5B [SEQ ID No. 3], fragments thereof or the antisense sequence, expressible in plants. Included within the scope of a gene encoding the GA4 amino acid sequence of FIGS. 4A–4B [SEQ ID No. 2] are functional derivatives of the GA4 sequence of the invention, as well as variant, analog, species, allelic and mutational derivatives.

As used herein, modulation of GA4 expression entails the enhancement or reduction of the naturally occurring levels of the protein. Specifically, the translation of RNA encoding GA4 can be reduced using the technique of antisense cloning.

In general, antisense cloning entails the generation of an expression module which encodes an RNA complementary (antisense) to the RNA encoding GA4 (sense). By expressing the antisense RNA in a cell which expresses the sense strand, hybridization between the two RNA species will occur resulting in the blocking of translation. Alternatively, overexpression of the GA4 protein might be accomplished by use of appropriate promoters, enhancers, and other modifications. Those of skill in the art would be aware of references describing the use of antisense genes in plants (van der Krol et al., *Gene* 72:45–50 (1988); van der Krol et al., *Plant Mol. Biol.* 14:467–486 (1990); Zhang et al., *Plant Cell* 4:1575–1588 (1992)).

Other foreign marker genes (i.e., exogenously introduced genes) typically used include selectable markers such as a Leo gene (Potrykus et al., *Mol. Gen. Genet* 199:183–188 (1985)) which codes for kanamycin resistance; a bar gene which codes for bialaphos resistance; a mutant EPSP synthase gene (Hinchee et al., *Bio/technology* 6:915–922 (1988)) which encodes glyphosate resistance; a nitrilase gene which confers resistance to bromoxynil (Stalker et al., *J. Biol. Chem.* 263:6310–6314 (1988)); a mutant acetolactate synthase gene (ALS) which confers imidazolinone or sulphonylurea resistance (EP application number 154,204); a methotrexate resistant DHFR gene (Thillet et al., *J. Biol. Chem.* 263:12500–12508) and screenable markers which include β-glucuronidase (GUS) or an R-locus gene, alone or in combination with a C-locus gene (Ludwig et al., *Proc. Natl. Acad. Sci. USA* 86:7092 (1989); Paz-Ares et al., *EMBO J.* 6:3553 (1987)).

Alternatively, the genetic construct for expressing the desired protein can be microinjected directly into plant cells by use of micropipettes to mechanically transfer the recombinant DNA. The genetic material may also be transferred into plant cells using polyethylene glycol to form a precipitation complex with the genetic material that is taken up by cells. (Paszkowski et al., *EMBO J.* 3:2717–22 (1984)). The desired gene may also be introduced into plant cells by electroporation. (Fromm et al., "Expression of Genes Transferred into Monocot and Dicot Plant Cells by Electroporation," *Proc. Natl. Acad. Sci. U.S.A.* 82:5824 (1985)). In this technique, plant protoplasts are electroporated in the presence of plasmids containing the desired genetic construct. Electrical impulses of high field strength reversibly permeabilize biomembranes allowing the introduction of plasmids. Electroporated plant protoplasts reform cell walls, divide, and form plant calli. Selection of the transformed plant cells expressing the desired gene can be accomplished using phenotypic markers as described above.

Another method of introducing the desired gene into plant cells is to infect the plant cells with *Agrobacterium tumefaciens* transformed with the desired gene. Under appropriate conditions well-known in the art, transformed plant cells are grown to form shoots, roots, and develop further into plants. The desired genetic sequences can be joined to the Ti plasmid of *Agrobacterium tumefaciens*. The Ti plasmid is transmitted to plant cells on infection by *Agrobacterium tumefaciens* and is stably integrated into the plant genome. Horsch et al., "Inheritance of Functional Foreign Genes in Plants," *Science* 233: 496 498 (1984); Fraley et al., *Proc. Nat'l Acad. Sci. U.S.A.* 80: 4803 (1983)); Feldmann, K. A. et al., *Mol. Gen. Genet.,* 208: 1–9 (1987); Walden, R. et al., *Plant J.,* 1: 281–288 (1991).

Presently there are several different ways to transform plant cells with Agrobacterium:
 (1) co-cultivation of Agrobacterium with cultured, isolated protoplasts, or
 (2) transformation of cells or tissues with Agrobacterium.

Method (1) requires an established culture system that allows culturing protoplasts and plant regeneration from cultured protoplasts. Method (2) requires that the plant cells or tissues can be transformed by Agrobacterium and that the transformed cells or tissues can be induced to regenerate into whole plants. In the binary system, to have infection, two plasmids are needed: a T-DNA containing plasmid and a vir plasmid.

Routinely, however, one of the simplest methods of plant transformation is explant inoculation, which involves incubation of sectioned tissue with Agrobacterium containing the appropriate transformation vector (Plant Genetic Transformation and Gene Expression, A Laboratory Manual, Oxford: Blackwell Scientific Publications (1988); Walden, Genetic Transformation in Plants, Milton Koynes: Open University Press (1988)).

All plants from which protoplasts can be isolated and cultured to give whole regenerated plants can be used for the expression of the desired gene. Suitable plants include, for example, species from the genera Fragaria, Lotus, Medicago, Onobrychis, Trifolium, Trigonella, Vigna, Citrus, Linum, Geranium, Manicot, Daucus, Airabidopsis, Brassica, Raphanus, Sinapis, Atropa, Capsicurm, Datura, Hyosyanmus, Lycopersion, Nicotiana, Solanum, Petunia, Digitalis, Majorana, Cichorium, Helianthus, Lactuca, Bromus, Asparagus, Antirrhinum, Henerocallis, Nemesia, Pelargonium, Panicum, Pennisetum, Ranunculus, Senecio, Salpiglossis, Cucumis, Browallia, Glycine, Lolium, Zea, Triticum, Sorghum, and Datura. Additional plant genera that may be transformed by Agrobacterium include Ipomoea, Passiflora, Cyclamen, Malus, Prunus, Rosa, Rubus, Populus, Santalum, Allium, Lilium, Narcissus, Ananas, Arachis, Phaseolus, and Pisum.

Plant regeneration techniques are well known in the art and include those set forth in the *Handbook of Plant Cell Culture*, Volumes 1–3, Eds. Evans et al. Macmillan Publishing Co., New York, N.Y. (1983, 1984, 1984, respectively); Predieri and Malavasi, *Plant Cell, Tissue, and Organ Culture* 17:133–142 (1989); James, D. J., et al., *J. Plant Physiol.* 132:148–154 (1988); Fasolo, F., et al., *Plant Cell, Tissue, and Organ Culture* 16:75–87 (1989); Valobra and James, *Plant Cell, Tissue, and Organ Culture* 21:51–54 (1990); Srivastava, P. S., et al., *Plant Science* 42:209–214 (1985); Rowland and Ogden, *Hort. Science* 27:1127–1129 (1992); Park and Son, *Plant Cell, Tissue, and Organ Culture* 15:95–105 (1988); Noh and Minocha, *Plant Cell Reports* 5:464–467 (1986); Brand and Lineberger, *Plant Science* 57:173–179 (1988); Bozhkov, P. V., et al., *Plant Cell Reports* 11:386–389 (1992); Kvaalen and von Arnold, *Plant Cell, Tissue, and Organ Culture* 27:49–57 (1991); Tremblay and Tremblay, *Plant Cell, Tissue, and Organ Culture* 27:95–103 (1991); Gupta and Pullman, U.S. Pat. No. 5,036,007; Michler and Bauer, *Plant Science* 77:111–118 (1991); Wetzstein, H. Y., et al., *Plant Science* 64:193–201 (1989); McGranahan, G. H., et al., *Bio/Technology* 6:800–804 (1988); Gingas, V. M., *Hort. Science* 26:1217–1218 (1991); Chalupa, V., *Plant Cell Reports* 9:398–401 (1990); Gingas and Lineberger, *Plant Cell, Tissue, and Organ Culture* 17:191–203 (1989); Bureno, M. A., et al., *Phys. Plant.* 85:30–34 (1992); and Roberts, D. R., et al., Can. J. Bot. 68:1086–1090 (1990).

Plant regeneration from cultured protoplasts is described in Evans et al., "Protoplast Isolation and Culture," in *Hand-* book of Plant Cell Culture 1:124–176 (MacMillan Publishing Co., New York, 1983); M. R. Davey, "Recent Developments in the Culture and Regeneration of Plant Protoplasts," Protoplasts, 1983 - Lecture Proceedings, pp. 19–29 (Birkhiauser, Basel, 1983); P. J. Dale, "Protoplast Culture and Plant Regeneration of Cereals and Other Recalcitrant Crops," in Protoplasts 1983 - Lecture Proceedings, pp. 31–41 (Birkhauser, Basel, 1983); and H. Binding, "Regeneration of Plants," in Plant Protoplasts, pp. 21–37 (CRC Press, Boca Raton, 1985).

Techniques for the regeneration of plants varies from species to species but generally, a suspension of transformed protoplasts containing multiple copies of the desired gene is first provided. Embryo formation can then be induced from the protoplast suspensions, to the stage of ripening and germination as natural embryos. The culture media will generally contain various amino acids and hormones, such as auxins and cytokinins. It is also advantageous to add glutamic acid and proline to tile medium, especially for such species as corn and alfalfa.

Mature plants, grown from transformed plant cells, are selfed to produce an inbred plant. The inbred plant produces seed containing the recombinant DNA sequences promoting increased expression of GA4.

Parts obtained from regenerated plants, such as flowers, seeds, leaves, branches, fruit, and the like are covered by the invention provided that these parts comprise the herbicidal tolerant cells. Progeny and variants, and mutants of the regenerated plants are also included within the scope of this invention. As used herein, variant describes phenotypic changes that are stable and heritable, including heritable variation that is sexually transmitted to progeny of plants, provided that the variant still comprises a herbicidal tolerant plant through enhanced rate of acetylation. Also, as used herein, mutant describes variation as a result of environmental conditions, such as radiation, or as a result of genetic variation in which a trait is transmitted meiotically according to well-established laws of inheritance.

Plants which contain the GA4 encoding DNA of the invention and no other foreign marker gene are advantageous in that removal of the foreign marker gene, once inserted into the plant, may be impossible without also removing the GA4 gene. Absence of the foreign marker gene is sometimes desired so as to minimize the number of foreign genes expressed. This can be achieved by providing the GA4-encoding DNA between Ti-plasmid borders.

The T-DNA insertion mutant, ga4-2 and the EMS-induced mutant, ga4-1 both contain sequence alterations in the gene. The changes in the mutant alleles interfere with normal transcription. The deduced amino acid sequence of the GA4 protein shows similarity to the sequences of flavanolne-3-hydroxylase and ACC oxidase from a variety of plant species (Meldgaard, M., Theor. Appl. Genet. 83: 695–706 (1992); Britsch, L. et al., J. Bio. Chem. 8:5380–5387 (1992); Deikmann, J. et al., EMBO J. 7: 3315–3320 (1988)).

The GA4 gene product is believed to be a 3-β-hydroxylase. The 3-β-hydroxylase is critical for controlling stem growth (Ingram et al., Planta 160: 455–463 (1984). Accordingly, the GA4 of the invention may be applied to crops to enhance and facilitate such stem elongation, flowering and fruiting. Alternatively, the DNA encoding GA4 may be genetically inserted into the plant host.

All plants which can be transformed are intended to be hosts included within the scope of the invention (preferably, dicotyledonous plants). Such plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhinum, Hererocallis, Nernesia, Pelargonium, Panicum, Pennisetum, Ranunculus, Sencia, Salpiglossis, Cucurnis, Browalia, Glycine, Lolium, Zea, Triticum, Sorghum, Malus, Apium, Datura, the le mutant in peas, the ga4 mutant in Arabadopsis, and the dwarf- mutant in Monocotyledonous plants such as corn.

Examples of commercially useful agricultural plants useful in the methods of the invention as transgenic hosts containing the GA4 DNA or antisense sequence of the invention include grains, legumes, vegetables and fruits, including but not limited to soybean, wheat, corn, barley, alfalfa, cotton, rapeseed, rice, tobacco, rye, tomatoes, beans, peas, celery, grapes, cabbage, oilseed, apples, strawberries, mulberries, potatoes, cranberries and lettuce.

Having now generally described the invention, the same will be more readily understood through reference to the following examples which are provided by way of illustration, and are not intended to be limiting of the present invention, unless specified.

EXAMPLES

EXAMPLE 1

Methods

Plants and RNA and DNA Isolation

The ga4 mutant was obtained from M. Koornneef (Agricultural University, Wageningen, The Netherlands). T-DNA tagged ga4 mutant was generated by Agrobacterium root transformation with tile pBIN19 vector (Bevan, M., Nucl. Acids. Res. 12:8711–8721 (1984)) (Clontech, Palo Alto, Calif. as "pBin19 in MC1022"). A description of T-DNA tagging and insertional mutagenesis is found in Walden et al., Plant J., 1:281–288 (1991); Meinke, Dev. Gen., 12:382–392 (1991). Plants were grown under greenhouse conditions using a 16-hr light/8-hr dark cycle. Tissue for DNA and RNA isolation was harvested at approximately 3–4 weeks after planting and before bolting, frozen into liquid nitrogen and stored at −70° C. Genomic DNA was isolated using the methods of Watson, J. C. et al., DNA. Methods. Enzymol. 118:57–75 (1986). Total RNA was isolated using the methods of Ausubel, F. M. et al., Current protocols in Molecular Biology, New York: Green Publishing Associates Wiley Interscience (1989).

Library Construction and Screening

The genomic library for tile T-DNA insertion mutant, ga4 2, was constructed in λ FIX II vectors (Stratagene, La Jolla, Calif.—see Stratagene Undigested Lambda FIXII Vector Cloning Kit Instruction Manual) and packaged using Gigapack II Gold packaging extracts (Stratagene). The ga4-2 and Landsberg genomic libraries and Landsberg cDNA library were plated on E. coli strain ER1458 (New England Biolabs (Beverly, Mass.) - Cat. No. 401-C, pp. 202–203.) (Also see Raleigh, E. A., Meth. Enzymol., 152: 130–141 (1987) and Bullock, W. O. et al., Bio Techniques, 5:376–378 (1987).) Alternatively, Arabidopsis genomic and cDNA libraries may be obtained from the Arabidopsis Biological Resource Center, Ohio State University. The genomic library can be plated on E. coli strain NM554 and the cDNA library can be plated on E. coli strain Y1090 (both from Stratagene).

The DNA genomic library may be obtained as follows. One begins with a CsCI DNA preparation and partially digests it with Sau3AI. After digestion, a partial fill-in reaction is performed. The reaction mixture for the partial fill-in is as follows.

40 µl DNA

6 µl Sau3AI buffer 10x 2.5 µl 0.1 M DTT

1 µl 100 mM dATP

1 µl 100 mM dGTP

5 µl Klenow enzyme 4.5 µl H2O

After 30 minutes at 37° C. the reaction is terminated with phenol-chloroform and the DNA is obtained. The DNA is then loaded on a 0.7% low melting point agarose gel and after electrophoresing, bands between 10 and 23 kb are cut out from the gel. The gel with the cut-out bands is then melted at 67° C. The isolated DNA is then placed in the following ligation mixture:

2 µl Lambda Fix II, pre-digested arms (2 µg)

1 µg genomic DNA, partial fill-in 0.5 µl 10xligation buffer 0.5 µl 10 mM ATP (pH 7.05)

0.5 µl T4 DNA ligase

~1.5 µl H$_2$O (to 5 µl final volume)

Following ligation overnight at 4° C., the DNA is packaged using GIGAPACK II GOLD.

Plaque lifts were made using Hybond filters (Amersham Corp.), which were then autoclaved for 2 min. Filters were hybridized with probes as described for DNA and RNA gel blot analysis below.

DNA Subcloning and Sequencing

Bacteriophage λ DNA was prepared from ER1458 lysates according to the mini-prep method of Grossberger, D., *Nucl. Acids. Res.* 15:6737 (1987). DNA fragments were subcloned into pBluescript KS vectors (Stratagene) and used to transform JM109.

Double stranded DNA was isolated from plasmid clones and purified by CsCI banding. Sequencing was performed using α-$^{35}$S-dATP and Sequenase (United States Biochemical Corp.) according to the manufacture's protocol for double stranded DNA sequencing. Sequence analysis was performed using the Sequence Analysis Software package (Genetics Computer Group, Inc., Madison, Wis.) and the Blast network service of the National Center for Biotechnology Information (Bethesda, Md.).

DNA and RNA Gel Blot Analysis

Electrophoresis of DNA was in Tris-Acetate-EDTA buffer with subsequent transfer in 25 mM NaHPO$_4$ to Biotrans filters (International Chemical and Nuclear Corp.). Electrophoresis of RNA samples was in agarose gels containing RNAase inhibitor using MOPS/EDTA buffer and transferred to filters as for DNA. Filters were UV-crosslinked using a Stratalinker (Stratagene) and baked for 1 hr at 80° C.

Radioactive probes were separated from unincorporated nucleotides using a 1-ml Sephadex G-50 spin column and denatured in a microwave oven (Stroop, W. G. et al., *Anal. Biochem.* 182:222–225 (1989)). Prehybridization for 1 hr and hybridization overnight were performed at 65° C. in the hybridization buffer described by Church, G. M. et al., *Proc. Natl. Acad. Sci. USA* 81:1991–1995 (1984)). Filters were washed once for 15 min in 2xSSC at room temperature, then two times for 30 mill in 0.1 xSSC and 0.1% SDS at 60° C. The damp filters were autoradiographed at −80° C. using intensifying screens. Filters were stripped twice in 2 mM Tris-HCI, pH8.0, 1 mM EDTA, 0.2% SDS at 70° C. for 30 min prior to reprobing (Church, G. M. et al., *Proc. Natl. Acad. Sci. USA* 81:1991–1995 (1984)).

Example 2

Characterization of a Semidwarf T-DNA Insertion Mutant Allelic to ga4.

A semidwarf mutant was generated from Arabidopsis thaliana (Landsberg erecta) as a result of Agrobacterium tumefaciens-mediated root transformation (Valvekens, D. et al., *Proc. Natl. Acad. Sci. USA* 85:5536–5540 (1988)). This mutant transgenic plant elongates its shoots in response to exogenously added GA$_3$ (FIG. 1). The complemeentationi analysis of tile ga4-2 plant with ga4-1 plant (ga4xT) revealed that tile transgenic plant has an insertion mutation that is an allele of the ga4 locus. There are several different gibberellin-responsive mutants in Arabidopsis, and therefore to test for allelism the transgenic plant was crossed to them in pairwise combination. Complementation analysis with the other genetically characterized semidwarf mutants in Arabidopsis revealed that the cross between the transgenic plant and the EMS-induced ga4 plant (Koornneef, M. et al., *Theor. Appl. Genet.* 58:257–263 (1980)) does not complement the mutant phenotype (FIG. 1). Therefore the mutation in the transgenic plant is an allele of the ga4 locus.

To test for co-segregation of the mutant phenotype and the T-DNA insert, the T1 progeny of the transgenic mutant that exhibited the semidwarf trait were outcrossed to either an Arabidopsis tt2 plant or to wild type C24 (Arabidopsis Biological Resource Center - Ohio State University). One of skill in the art, however, would know that any *Arabidopsis thaliana* could be used to perform the out-cross to ga4-2 to obtain the F1 progeny. The self-fertilized F2 progeny from those two crosses were tested for segregation of the kanamycin resistance marker encoded by the T-DNA. Progeny were grown on sterile medium containing 50 mg/L kanamycin, and the ratio of kanamycin resistant plants to sensitive plants was determined by their viability. As approximately three quarters of the F2 progeny from both crosses are resistant to kanamycin (Table I) the data indicates that there is one T-DNA insertion site in the transgenic plant.

TABLE I

Segregation Ratios of the F2 Progeny from ga4-2 (T-DNA tagged allele) Plants Crossed to tt2 Plants or Crossed to C24 Wild Type Plants

| F2 Plant | Kan$^r$:Kan$^s$ | Approximate Segregation Ratios | T-DNA Insertions |
| --- | --- | --- | --- |
| ga4-2 x tt2 | 163:56 | 3:1 | 1 (P>0.8) |
| ga4-2 x C24 | 104:29 | 3:1 | 1 (P>0.3) |

Progeny were grown on sterile mineral nutrient medium containing 50 mg/L kanamycin; the ratio of kanamycin resistant plants to sensitive plants was determined from their viability. The number of T-DNA insertion sites predicted from the 3:1 segregation ratio and their probabilities from the Chi-square test are shown.

The self-fertilized F2 progeny from the two crosses were also tested for segregation of the mutant phenotype. The result from both crosses (Table II) shows a quarter of the resulting F2 progeny exhibit the semidwarf phenotype, indicating that the semidwarf phenotype is inherited as a single recessive mutation.

TABLE II

Segregation Ratios of the F2 Progeny from ga4-2 (T-DNA tagged allele) Plants Crossed to tt2 Plants or Crossed to C24 Wild Type Plants

| F2 Plant | Wild Type:Dwarf | Approximate Segregation Ratios | Mutant Loci |
|---|---|---|---|
| ga4-2 × tt2 | 151:53 | 3:1 | 1 (P>0.5) |
| ga4-2 × C24 | 74:25 | 3:1 | 1 (P>0.9) |

Progeny were soil grown and the ratio of plants that showed wild type compared to semidwarf phenotype were determined. The number of mutant loci predicted from the 3:1 segregation ratio and their probabilities from the Chi-square test are shown.

Although the data from these two independent tests are indicative, they are not sufficient to conclude that the ga4 allele is tagged by the T-DNA insert. The presence of the insert and its linkage with the mutant trait was therefore further tested by DNA gel blot analysis.

Example 3

DNA Gel Blot Analysis

Figure 2:
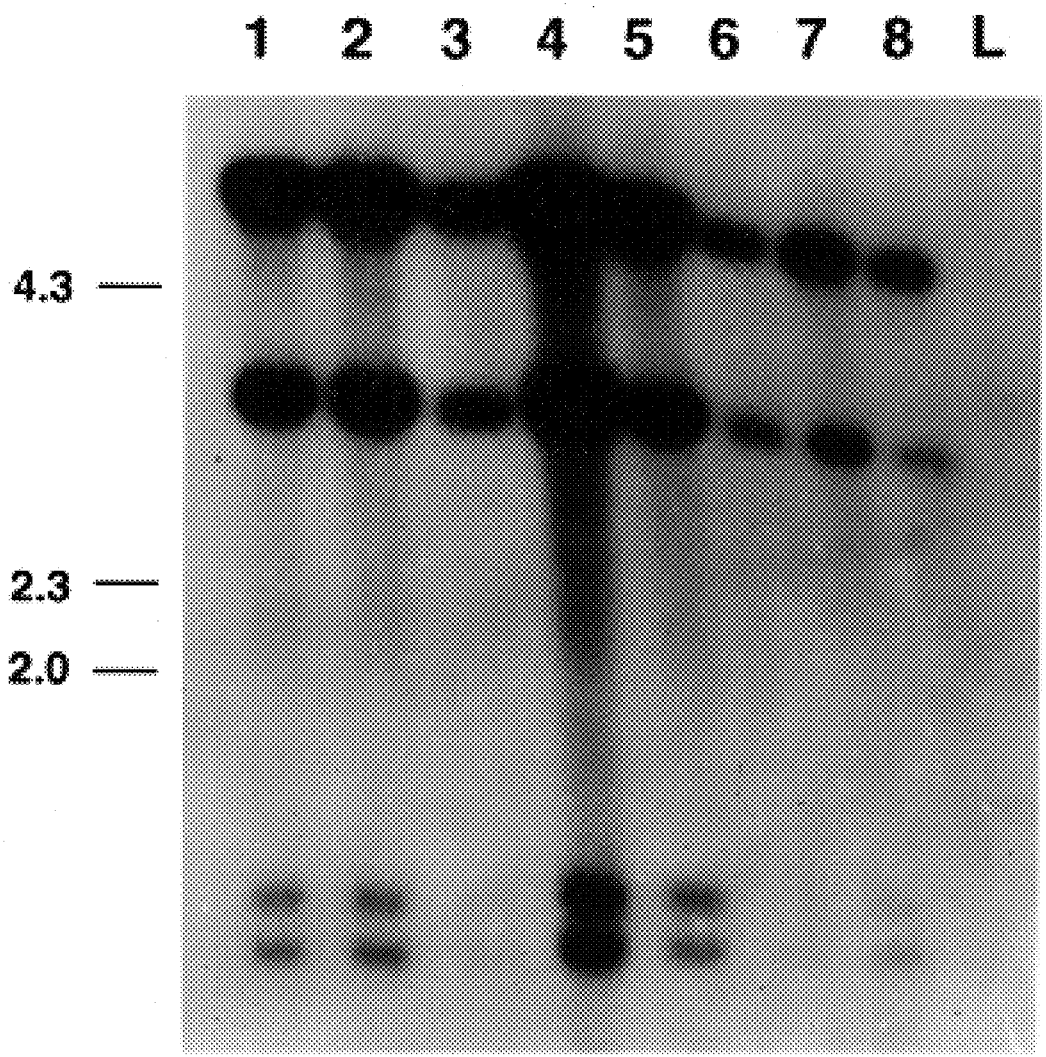
FIG. 2: DNA gel blot hybridization analysis showing cosegregation of the T-DNA insert with the ga4 mutation. DNA, isolated from leaf tissue of F3 progeny of individual F2 (ga4-2×tt2 ) plants exhibiting the semidwarf phenotype, is shown in lanes 1-8, (8 samples). Four fragments associated with the T-DNA insert were visible in DNA from all plants. Molecular weight DNA size markers are shown in Kb. L, canonical, wild type, Landsberg er.

Twenty F3 progeny from self-fertilized F2 plants (transgenic plant×tt2) were selected for their semidwarf phenotype and were then further tested for linkage of the T-DNA insert and the mutant phenotype by DNA gel blot analysis. DNA was isolated from leaf tissue of the individual F3 progeny, digested with HindIII and, after separation on an agarose gel and transfer, the DNA gel blot was probed with $^{32}$P-labeled pBIN19 plasmid containing the T-DNA border sequences (Bevan, M., *Nucl. Acids. Res.* 12:8711–8721 (1984)). The probe hybridizes to DNA from all the representative transgenic plants confirming the presence of the T-DNA insert (FIG. 2). For the results shown in FIG. 2, the DNA was digested with HindIII, separated by electrophoresis, bound to nylon filters, and then hybridized to $^{32}$P-labeled pBIN19 plasmid which contains the T-DNA border sequences. The hybridization pattern correlates with the T-DNA insert and the T-DNA/plant junctions. Four fragments associated with the T-DNA insert were visible in all plants (lanes 1–8) (FIG. 2) and cosegregate with the semidwarf phenotype. Therefore, the insertion site contains a complex T-DNA unit. There is no hybridization with the wild type (Landsberg er) control. Thus, analysis from both the segregation test (Tables I and II) and the DNA gel blot analysis (FIG. 2), indicate that the T-DNA insert is the cause of the semidwarf mutation in the transgenic plant (the T-DNA tagged allele will be referred to as ga4-2) and that the T-DNA insert is tightly linked to the ga4 locus (the EMS-induced allele will be referred to as ga4-1).

Example 4

Isolation of the GA4 Gene

Figure 3A:
FIGS. 3A–3B: Restriction map of the genomic clones (γT1-5 and γWT6) and subclones (pT12, pT34, and pWT32) used to isolate the GA4 gene. H, HindIII restriction site.

A genomic library was constructed with DNA isolated from F4 progeny of the ga4-2 plant. All constructs were subcloned into pBluescript KS. The genomic clone, λT1-5, was derived by screening the ga4-2 genomic library Using $^{32}$P-labeled pBIN19 vector as a probe. After plaque purification, clone λT1 5 was characterized by restriction enzyme analysis (FIG. 3A). The 1.2-kb HindIII fragment subclone, pT12, contains the T-DNA/plant DNA junction and was used to identify the insertion site by sequencing into the T-DNA insertion break point.

The genomic clone, λWT6, was derived as follows. The subclone pWT32 which was deposited in a bacterial host with the American Type Culture Collection ("ATCC"), 12301 Park Lawn Drive, Rockville, Md. 20852, on Apr. 4, 1997 (ATCC Deposit No. 98394), and which corresponds to the T-DNA insertion site in λT-15 was used as a probe to screen the leaf cDNA library and the ga4-1 genomic library.

Figure 3B:

To identify the region that corresponds to the T-DNA insertion site, the HindIII fragments of the genomic clone were subcloned into the plasmid vector pBluescript KS. The 1.2 Kb HindIII fragment subclone, pT12, contains the T-DNA/plant DNA junction and was used to identify the insertion site by sequencing into the T-DNA insertion break point. The plant sequences from the flanking 3.4 Kb HindIII fragment subclone, pT34, which was deposited in a bacterial host with the American Type Culture Collection ("ATCC"), 12301 Park Lawn Drive, Rockville, Md. 20852, on Apr. 4, 1997 (ATCC Deposit No. 98393) were used to isolate the corresponding wild type genomic clone, λWT6 (FIG. 3B). The 3.2 Kb HindIII subclone from λWT6 contains the sequences corresponding to the T-DNA insertion site in λT1-5 and was used as a probe to screen the leaf cDNA library and the ga4-1 genomic library. The isolated full length ga4 genomic and cDNA clones span sequences contained in both clone pT34 which was deposited in a bacterial host with the American Type Culture Collection ("ATCC"), 12301 Park Lawn Drive, Rockville, Md. 20852, on Apr. 4, 1997 (ATCC Deposit No. 98393), and pWT32 which was deposited in a bacterial host with the American Type Culture Collection ("ATCC"), 12301 Park Lawn Drive, Rockville, Md. 20852, on Apr. 4, 1997 (ATCC Deposit No. 98394).

Example 5

Nucleotide and Amino Acid Sequences

The GA4 cDNA is 1221 nucleotides with an open reading frame of 358 amino acids (FIGS. 4A–4B; SEQ ID No. 1 and SEQ ID No. 2). There is a single 433-base-pair intron whose position was deduced from a comparison of the cDNA and genomic sequences (SEQ ID No. 3). Sequence analysis of the T-DNA/plant DNA junction indicates that the T-DNA insertion is within the intron. Analysis of the sequence revealed two possible AUG initiation codons (nucleotide position 67 and nucleotide position 76) within the open reading frame, both of which have weak homology to the "Kozak" consensus sequence for translation initiation (Kozak, M., *Nucl. Acids Res.* 15:8125–8148 (1987); Lüteke, H. A. et al., *EMBO J.* 6:43–48 (1987).

To confirm that the sequence determined is indeed the GA4 locus, genomic fragments from the other allele, ga4-1, were isolated and sequenced. The ga4-1 allele was generated by EMS mutagenesis in the same genetic background, Landsberg er. Sequence analysis of ga4-1 indicates that the EMS-induced mutation occurs at nucleotide 725 (FIGS. 4A–4B) resulting in a single nucleotide change from G to A and a corresponding amino acid change from cysteine to tyrosine. This nucleotide change in the coding region, leading to the amino acid change, is presumably responsible for the ga4-1 mutation.

An alignment of the amino acid sequence of GA4 to barley flavanone-3-hydroxylase (F3H) [SEQ ID No. 4] exhibits a 32% amino acid identity (FIG. 6). FIG. 6 shows this alignment for the deduced amino acid sequences of the GA4 gene from Arabidopsis and flavanone-3-hydroxylase (F3H) from barley (Meldgaard, M., *Theor. Appl. Genet.* 83:695–706 (1992)). In addition, alignment to the amino acid sequence of 1-aminocyclopropane-1-carboxylate oxidase (ethylene-forming enzyme) from petunia shows 30% amino acid identity (data not shown).

On the basis of this sequence similarity, it is concluded that the GA4 gene encodes an hydroxylase involved in GA biosynthesis, and specifically a 3-β-hydroxylase. This conclusion agrees with information based on biochemical studies (Talon, M. et al., *Pmoc. Natl. Acad. Sci. USA* 87:7983–7987 (1990)) that showed that the Arabidopsis ga4 mutant had reduced levels of the 3-hydroxy- and 3,13-hydroxy-GAs, and that it accumulates the 13-hydroxy-GAs and the non-3,13-hydroxy-GAs, with some exceptions. Due to the ubiquitous nature of gibberellin growth factors, it is likely that a similar activity and gene sequence will be found for the cognate genes corresponding to GA4 in agronomically important crop plants, such as, for example, corn, peas, barley, potato, radish, rapeseed, alfalfa, celery, grapes, cabbage, lettuce, carrots, cucumber, squash, watermelon, rice and beans.

Example 6

The ga4 Mutant Overexpresses ga4 mRNA

Figure 7:
FIG. 7: RNA gel blot analysis of GA4 gene expression in different tissues (silique, flower, root and leaf) of Arabidopsis.
Figure 8:
FIG. 8: RNA gel blot analysis of ga4 and GA4 gene expression in Arabidopsis in 4-week-old rosette leaves of T-ga4 (ga4-2), ga4 (ga4-1) and Lan (Landsberg, er).

To study the pattern of GA4 gene expression, total RNA was isolated from different tissue types and RNA gel blots were hybridized with a $^{32}$P-labeled PCR GA4 specific probe. A 1.4 Kb transcript is seen in root, flower, and siliques (FIG. 7). The same size transcript was detected in leaves when more RNA is loaded on the gel. This data is shown in FIG. 8—the "Lan" sample. The gene is expressed ubiquitously in the different tissues examined (root, leaf, flower and silique), but the message is most abundant in the silique.

Figure 9:
FIG. 9: RNA gel blot analysis of GA4 gene expression in Arabidopsis in ga4-1 with (+) or without (−) exogenous $GA_3$. The ga4-1 plants were sprayed with $10^{-5}$M $GA_3$ and leaf samples were taken 8 and 24 hours after the treatment.

There is differential expression in 4-week-old rosette leaves between the wild type and mutants. There is 3 to 4 fold more message expressed in the EMS induced ga4-1 plants as compared to wild type, but no message is detected in the T-DNA tagged ga4-2 plants (FIG. 8). The over-expression of ga4 message, detected in the ga4-1 plants, can be repressed by the application of $10^{-5}$M exogenous GA$_3$ Ott the rosette leaves of Arabidopsis. The transcriptional repression can be detected at 8 hours after the initial treatment and lasts for up to 24 hours (FIG. 9).

The over-expression of ga4 message in the EMS-induced ga4-1 mutant and transcriptional regulation by exogenous GA$_3$ is a novel finding as regards the regulation of the gibberellin biosynthesis pathway. The terminal gibberellins in Arabidopsis are GA$_1$ and GA$_4$, which are effective in causing stem elongation (Talon, M. et al., *Proc. Natl. Acad. Sci. USA* 87:7983–7987 (1990)). GA$_3$ has been shown to be present at low levels in vegetative tissue of maize. GA$_3$ is biosynthesized from GA$_{20}$ via GA$_5$;and GA$_1$ is the product of GA$_3$ in Maize (Fujioka, S. et al., *Plant Physiol.* 94:127–131(1990)). There is no evidence of GA$_3$ biosynthesis in Arabidopsis, but experiments show that exogenous GA$_3$ is active in promoting stem elongation in Arabidopsis and in other species, for example, maize, cabbages, beans, rice, peas, watermelons, squash and cucumbers. The biological activity may be induced by either GA$_3$ itself or the terminal GAs, such as GA$_1$, as shown in the proposed pathway in maize (Fujioka, S. et al., *Plant Plysiol.* 94:127–131 (1990)). In wild type plants, the concentrations and proportions of the cellular gibberellins are maintained by the balance between synthesis and utilization. In the ga4-1 plant, this balance is perturbed by the mutation and the concomitant reduction in the catalytic activity of the 3 -β-hydroxylase which leads to the accumulation of GA$_9$ and GA$_{20}$ and the reduction in GA$_4$ and GA$_1$, respectively. The mutated gene would either lead to translation of the mutant form of the protein (presumably inactive or less active) or to no translation at all. The over-expression of ga4 message as detected in the ga4-1 plants and the repression of transcription by exogenous GA$_3$ indicates a transcriptional feedback regulatory mechanism. One hypothesis to explain these results in the ga4-1 plants is that the regulatory domain of the GA4 protein is intact but the reduced levels of endogenous GA$_4$ and GA$_1$ diminish the feedback control by the terminal GAs and the application of exogenous GA$_3$, which leads to the accumulation of terminal GAs in Arabidopsis, restores the feed-back mechanism.

It has been previously established that 3-β-3-hydroxylation is important in the regulation of stem growth (Ingram, T. J. et al., *Planta* 160:455–463 (1984)). Our results indicate that, in addition to the critical roles the properties and compartmentalization of the active GAs play in stein growth, molecular regulatory mechanisms also play an important part in the control of gibberellin biosynthesis.

Example 7

Expressing the GA4 Protein

The GA4 protein is expressed by transforming a host with the DNA construct of SEQ ID No. 1 or SEQ ID No. 3 or a DNA construct comprising DNA encoding the amino acid sequence of SEQ ID No. 2 operably linked to a promoter. The GA4 protein is expressed from the construct in the transformed host cell.

Example 8

Gene Expression in a Plant

The expression of a gene in a plant is directed such that the gene has the same temporal and spatial expression pattern of GA4. The gene is operably linked to the regulatory sequences of GA4 DNA to create an expression module, and a plant is then transformed with the expression module.

Example 9

Modulating the Translation of RNA Encoding GA4 Protein

The translation of RNA encoding GA4 protein in a plant is modulated by generating an expression vector encoding antisense GA4 RNA. The plant is then transfected with the expression vector encoding the antisense GA4 RNA.

Example 10

Cloning DNA Encoding GA4 Protein

A DNA molecule encoding the GA4 protein is cloned by hybridizing a desired DNA molecule to the sequences or antisense sequences of DNA SEQ ID No. 1 or DNA SEQ ID No.3 under stringent hybridization conditions. Those DNA molecules hybridizing to the probe sequences are selected and transformed into a host cell. The transformants that express GA4 are selected and cloned.

Example 11

Hybridization Conditions for Cloning DNA Encoding GA4 Protein

One possible set of hybridization conditions for the cloning of the DNA encoding GA4 protein is as follows:
1) prehybridizing for 1 hour;
2) hybridizing overnight at 65° C. in the hybridization buffer; and

Example 12

Stimulating Plant Stem Elongation

Plant stem elongation is stimulated by inserting the DNA construct encoding the amino acid sequence shown in FIG. 4 [SEQ ID No. 2] into a transgenic plant. The transgenic plant is produced by any of several methods known in the art including those previously described in this specification.

The stem elongation may be stimulated in Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhinum, Hererocallis, Nemesia, Pelargonium, Panicum, Pennisetum, Ranunculus, Sencia, Salpiglossis, Cucumis, Browalia, Glycine, Lolium, Zea, Triticum, Sorghum, Malus, Apium, and Datura.

Example 13

Producing Dwarf Plants

Dwarf plants are produced by blocking the GA4 gene by homologous recombination, or by transforming with a GA4 anti-sense DNA in order to produce transgenic plants. A cDNA sequence can be used to construct the antisense construct which is then transformed into a plant by using an Agrobacterium vector. (Zhang et al., *Plant Cell* 4: 1575–1588 (Dec. 1992)). Even partial antisense sequences can be used as antisense and can interfere with the cognate endogenous genes (van der Krol et al., *Plant Mol. Biol.* 14:457–466 (1990)). The plant is transformed with the antisense construct according to the protocol of Valvekens et al., *Proc. Natl. Acad, Sci, USA* 85:5536–5540 (1988).

Dwarf plants are known to be commercially valuable. For example, dwarf trees for apples, cherries, peaches, pears and nectarines are commercially available (Burpee Gardens Catalogue 1994, pages 122–123).

Example 13

Molecular Weight Markers

The GA4 protein produced recombinantly is purified by routine methods in the art (*Current Protocol in Molecular Biology*, Vol. 2, Chap. 10, John Wiley & Sons, Publishers (1994)). Because, the deduced amino acid sequence is known, the molecular weight of this protein can be precisely determined and the protein can be used as a molecular weight marker for gel electrophoresis. The calculated molecular weight of the GA4 protein based on the deduced amino acid sequence is 39.5 kDa.

CONCLUSIONS

We have obtained full length genomic and cDNA clones and the sequences for the GA4 protein. It is believed that the GA4 locus encodes an hydroxylase involved in gibberellin biosynthesis.

All references mentioned herein are incorporated by reference in the disclosure.

Having now fully described the invention by way of illustration and example for purposes of clarity and understanding, it will be apparent to those of ordinary skill in the art that certain changes and modifications may be made in the disclosed embodiments and such modifications are intended to be within the scope of the present invention.

What is claimed is:

1. A DNA Construct consisting essentially of DNA encoding the amino acid sequence of SEQ ID No. 2.

2. The DNA construct of claim 1, wherein said DNA is that of SEQ ID No. 1 or SEQ ID No. 3.

3. A DNA construct comprising DNA encoding the amino acid sequence of SEQ ID No. 2.

4. The DNA Construct of claim 3, wherein said DNA is that of SEQ ID No. 1 or SEQ ID No. 3.

5. A vector comprising the sequences of any one of claims 1–4.

6. A host transformed with the vector of claim 5, wherein said host is selected from the group consisting of bacteria, yeast and plants.

7. The host of claim 6, wherein said host is a plant cell.

8. The host of claim 7, wherein said plant cell is a dicotyledonous plant cell.

9. A plant regenerated from the plant cell of claim 7.

10. Progeny of the plant of claim 9.

11. A propagule of the plant of claim 10.

12. A seed produced by the progeny of claim 10.

13. A method for expressing CA4 protein, wherein said method comprises:
   1) transforming a host with the construct of any one of claims 1–4 operably linked to a promoter; wherein said host is selected from the group consisting of bacteria, yeast and plants;
   2) expressing said GA4 protein from said DNA on said construct in said transformed host cell.

14. A method of modulating the translation of RNA encoding GA4 in a plant comprising the steps of:
   1) generating an expression vector encoding antisense GA4 RNA;
   2) transfecting said plant with said expression vector of part (1).

15. An isolated DNA construct wherein said construct consists essentially of a nucleic acid sequence, and wherein said nucleic acid sequence:
   1) encodes a GA4 polypeptide, and
   2) hybridizes to the sense or antisense sequence of the DNA of SEQ ID No. 1 or SEQ ID No. 3 when hybridization is performed under stringent hybridization conditions.

16. An isolated DNA molecule encoding a GA4 protein, said DNA molecule prepared by a process comprising:
   1) hybridizing a desired DNA molecule to the sense or antisense sequence of DNA SEQ ID No. 1 or DNA SEQ ID No. 3, wherein the hybridization is performed under stringent hybridization conditions;
   2) selecting those DNA molecules of said population that hybridize to said sequence; and
   3) selecting DNA molecules of part (2) that encode said GA4 protein.

17. An isolated DNA molecule encoding a GA4 protein as claimed in claims 15 or 16, said DNA molecule prepared by a process comprising:
   1) prehybridizinig for 1 hour;
   2) hybridizing overnight at 65 °C. in the hybridization buffer; and
   3) washing once for 15 minutes in 2×SSC at room temperature, then two times for 30 minutes in 0.1×SSC and 0.1% SDS at 60° C.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1228 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 67..1140

(xi) SEQUENCE DESCRIPTION: SEQ ID NO:1:

```
ATAAGAAAAA AAACACAAAC ATCTATCAAA TTTACAAAGT TTTAAAACTA ATTAAAAAAG        60

AGCAAG ATG CCT GCT ATG TTA ACA GAT GTG TTT AGA GGC CAT CCC ATT         108
       Met Pro Ala Met Leu Thr Asp Val Phe Arg Gly His Pro Ile
         1               5                  10

CAC CTC CCA CAC TCT CAC ATA CCT GAC TTC ACA TCT CTC CGG GAG CTC         156
His Leu Pro His Ser His Ile Pro Asp Phe Thr Ser Leu Arg Glu Leu
 15                  20                  25                  30

CCG GAT TCT TAC AAG TGG ACC CCT AAA GAC GAT CTC CTC TTC TCC GCT         204
```

```
Pro Asp Ser Tyr Lys Trp Thr Pro Lys Asp Leu Leu Phe Ser Ala
             35              40              45

GCT CCT TCT CCT CCG GCC ACC GGT GAA AAC ATC CCT CTC ATC GAC CTC      252
Ala Pro Ser Pro Pro Ala Thr Gly Glu Asn Ile Pro Leu Ile Asp Leu
         50              55              60

GAC CAC CCG GAC GCG ACT AAC CAA ATC GGT CAT GCA TGT AGA ACT TGG      300
Asp His Pro Asp Ala Thr Asn Gln Ile Gly His Ala Cys Arg Thr Trp
         65              70              75

GGT GCC TTC CAA ATC TCA AAC CAC GGC GTG CCT TTG GGA CTT CTC CAA      348
Gly Ala Phe Gln Ile Ser Asn His Gly Val Pro Leu Gly Leu Leu Gln
     80              85              90

GAC ATT GAG TTT CTC ACC GGT AGT CTC TTC GGG CTA CCT GTC CAA CGC      396
Asp Ile Glu Phe Leu Thr Gly Ser Leu Phe Gly Leu Pro Val Gln Arg
 95             100             105             110

AAG CTT AAG TCT GCT CGG TCG GAG ACA GGT GTG TCC GGC TAC GGC GTC      444
Lys Leu Lys Ser Ala Arg Ser Glu Thr Gly Val Ser Gly Tyr Gly Val
             115             120             125

GCT CGT ATC GCA TCT TTC TTC AAT AAG CAA ATG TGG TCC GAA GGT TTC      492
Ala Arg Ile Ala Ser Phe Phe Asn Lys Gln Met Trp Ser Glu Gly Phe
             130             135             140

ACC ATC ACT GGC TCG CCT CTC AAC GAT TTC CGT AAA CTT TGG CCC CAA      540
Thr Ile Thr Gly Ser Pro Leu Asn Asp Phe Arg Lys Leu Trp Pro Gln
             145             150             155

CAT CAC CTC AAC TAC TGC GAT ATC GTT GAA GAG TAC GAG GAA CAT ATG      588
His His Leu Asn Tyr Cys Asp Ile Val Glu Glu Tyr Glu Glu His Met
     160             165             170

AAA AAG TTG GCA TCG AAA TTG ATG TGG TTA GCA CTA AAT TCA CTT GGG      636
Lys Lys Leu Ala Ser Lys Leu Met Trp Leu Ala Leu Asn Ser Leu Gly
175             180             185             190

GTC AGC GAA GAA GAC ATT GAA TGG GCC AGT CTC AGT TCA GAT TTA AAC      684
Val Ser Glu Glu Asp Ile Glu Trp Ala Ser Leu Ser Ser Asp Leu Asn
             195             200             205

TGG GCC CAA GCT GCT CTC CAG CTA AAT CAC TAC CCG GTT TGT CCT GAA      732
Trp Ala Gln Ala Ala Leu Gln Leu Asn His Tyr Pro Val Cys Pro Glu
             210             215             220

CCG GAC CGA GCC ATG GGT CTA GCA GCT CAT ACC GAC TCC ACC CTC CTA      780
Pro Asp Arg Ala Met Gly Leu Ala Ala His Thr Asp Ser Thr Leu Leu
         225             230             235

ACC ATT CTG TAC CAG AAC AAT ACC GCC GGT CTA CAA GTA TTT CGC GAT      828
Thr Ile Leu Tyr Gln Asn Asn Thr Ala Gly Leu Gln Val Phe Arg Asp
     240             245             250

GAT CTT GGT TGG GTC ACC GTG CCA CCG TTT CCT GGC TCG CTC GTG GTT      876
Asp Leu Gly Trp Val Thr Val Pro Pro Phe Pro Gly Ser Leu Val Val
255             260             265             270

AAC GTT GGT GAC CTC TTC CAC ATC CTA TCC AAT GGA TTG TTT AAA AGC      924
Asn Val Gly Asp Leu Phe His Ile Leu Ser Asn Gly Leu Phe Lys Ser
             275             280             285

GTG TTG CAC CGC GCT CGG GTT AAC CAA ACC AGA GCC CGG TTA TCT GTA      972
Val Leu His Arg Ala Arg Val Asn Gln Thr Arg Ala Arg Leu Ser Val
         290             295             300

GCA TTC CTT TGG GGT CCG CAA TCT GAT ATC AAG ATA TCA CCT GTA CCG     1020
Ala Phe Leu Trp Gly Pro Gln Ser Asp Ile Lys Ile Ser Pro Val Pro
     305             310             315

AAG CTG GTT AGT CCC GTT GAA TCG CCT CTA TAC CAA TCG GTG ACA TGG     1068
Lys Leu Val Ser Pro Val Glu Ser Pro Leu Tyr Gln Ser Val Thr Trp
320             325             330

AAA GAG TAT CTT CGA ACA AAA GCA ACT CAC TTC AAC AAA GCT CTT TCA     1116
Lys Glu Tyr Leu Arg Thr Lys Ala Thr His Phe Asn Lys Ala Leu Ser
335             340             345             350

ATG ATT AGA AAT CAC AGA GAA GAA TGATTAGATA ATAATAGTTG TGATCTACTA    1170
```

```
Met Ile Arg Asn His Arg Glu Glu
                355

GTTAGTTTGA TTAATAAATT GTTGTAAATG ATTTCAGCAA TATGATTTGT TTGTCCTC        1228

(2) INFORMATION FOR SEQ ID NO:2:

(i) SEQUENCE CHARACTERISTICS:
        (A) LENGTH: 358 amino acids
        (B) TYPE: amino acid
        (D) TOPOLOGY: linear (ii) MOLECULE TYPE: protein (xi) SEQUENCE DESCRIPTION: SEQ ID NO:2:

Met Pro Ala Met Leu Thr Asp Val Phe Arg Gly His Pro Ile His Leu
 1               5                  10                  15

Pro His Ser His Ile Pro Asp Phe Thr Ser Leu Arg Glu Leu Pro Asp
                20                  25                  30

Ser Tyr Lys Trp Thr Pro Lys Asp Leu Leu Phe Ser Ala Ala Pro
            35                  40                  45

Ser Pro Pro Ala Thr Gly Glu Asn Ile Pro Leu Ile Asp Leu Asp His
 50                      55                  60

Pro Asp Ala Thr Asn Gln Ile Gly His Ala Cys Arg Thr Trp Gly Ala
 65                      70                  75                  80

Phe Gln Ile Ser Asn His Gly Val Pro Leu Gly Leu Gln Asp Ile
            85                  90                  95

Glu Phe Leu Thr Gly Ser Leu Phe Gly Leu Pro Val Gln Arg Lys Leu
                100                 105                 110

Lys Ser Ala Arg Ser Glu Thr Gly Val Ser Gly Tyr Gly Val Ala Arg
            115                 120                 125

Ile Ala Ser Phe Phe Asn Lys Gln Met Trp Ser Glu Gly Phe Thr Ile
 130                 135                 140

Thr Gly Ser Pro Leu Asn Asp Phe Arg Lys Leu Trp Pro Gln His His
 145                 150                 155                 160

Leu Asn Tyr Cys Asp Ile Val Glu Glu Tyr Glu Glu His Met Lys Lys
            165                 170                 175

Leu Ala Ser Lys Leu Met Trp Leu Ala Leu Asn Ser Leu Gly Val Ser
            180                 185                 190

Glu Glu Asp Ile Glu Trp Ala Ser Leu Ser Ser Asp Leu Asn Trp Ala
            195                 200                 205

Gln Ala Ala Leu Gln Leu Asn His Tyr Pro Val Cys Pro Glu Pro Asp
 210                 215                 220

Arg Ala Met Gly Leu Ala Ala His Thr Asp Ser Thr Leu Leu Thr Ile
 225                 230                 235                 240

Leu Tyr Gln Asn Asn Thr Ala Gly Leu Gln Val Phe Arg Asp Asp Leu
            245                 250                 255

Gly Trp Val Thr Val Pro Pro Phe Pro Gly Ser Leu Val Val Asn Val
            260                 265                 270

Gly Asp Leu Phe His Ile Leu Ser Asn Gly Leu Phe Lys Ser Val Leu
            275                 280                 285

His Arg Ala Arg Val Asn Gln Thr Arg Ala Arg Leu Ser Val Ala Phe
            290                 295                 300

Leu Trp Gly Pro Gln Ser Asp Ile Lys Ile Ser Pro Val Pro Lys Leu
 305                 310                 315                 320

Val Ser Pro Val Glu Ser Pro Leu Tyr Gln Ser Val Thr Trp Lys Glu
            325                 330                 335
```

Tyr Leu Arg Thr Lys Ala Thr His Phe Asn Lys Ala Leu Ser Met Ile
    340                 345                 350

Arg Asn His Arg Glu Glu
    355

(2) INFORMATION FOR SEQ ID NO:3:

(i) SEQUENCE CHARACTERISTICS:
        (A) LENGTH: 1663 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

| | |
|---|---|
| ATAAGAAAAA AAACACAAAC ATCTATCAAA TTTACAAAGT TTTAAAACTA ATTAAAAAAG | 60 |
| AGCAAGATGC CTGCTATGTT AACAGATGTG TTTAGAGGCC ATCCCATTCA CCTCCCACAC | 120 |
| TCTCACATAC CTGACTTCAC ATCTCTCCGG GAGCTCCCGG ATTCTTACAA GTGGACCCCT | 180 |
| AAAGACGATC TCCTCTTCTC CGCTGCTCCT TCTCCTCCGG CCACCGGTGA AAACATCCCT | 240 |
| CTCATCGACC TCGACCACCC GGACGCGACT AACCAAATCG GTCATGCATG TAGAACTTGG | 300 |
| GGTGCCTTCC AAATCTCAAA CCACGGCGTG CCTTTGGGAC TTCTCCAAGA CATTGAGTTT | 360 |
| CTCACCGGTA GTCTCTTCGG GCTACCTGTC CAACGCAAGC TTAAGTCTGC TCGGTCGGAG | 420 |
| ACAGGTGTGT CCGGCTACGG CGTCGCTCGT ATCGCATCTT TCTTCAATAA GCAAATGTGG | 480 |
| TCCGAAGGTT TCACCATCAC TGGCTCGCCT CTCAACGATT TCCGTAAACT TTGGCCCCAA | 540 |
| CATCACCTCA ACTACTGGTA TATCTTTTAT ACACTCGATC CTATATACTT GTACTTGTGT | 600 |
| TTATTAGACC TTTTTCTACA TTAACAAAAA ACATATACAT AAGGACACAA TGTTTACATT | 660 |
| TAAGGTAGAA CATCCACAAA CGTTGGACGC CCTATAGGTA GTAACAAGGG GCATAGATAA | 720 |
| CAGAAGCAAC CGAAATTTGC CTTGTCCTCG GAGTTTAGTG GATTTAAGAG TTAAGTGCAT | 780 |
| AATGAAATCT AGTGTAGTAG TGGACCCAAC TCAAAGATTT TGAAGATATG TATTCTTTTA | 840 |
| ATCTTATCGG AGAAAACAAA ACAAAAAAAC AACAACTTGC TTTTCTATTT TATTTAAAGG | 900 |
| TCGTACAAAT ATTTAATGTA TGTATATGCA AATTGTGTCT AAATCTCATC TGTACTAATT | 960 |
| AGATGAATAC AATTCGTTTT TAATTAACAG CGATATCGTT GAAGAGTACG AGGAACATAT | 1020 |
| GAAAAAGTTG GCATCGAAAT TGATGTGGTT AGCACTAAAT TCACTTGGGG TCAGCGAAGA | 1080 |
| AGACATTGAA TGGGCCAGTC TCAGTTCAGA TTTAAACTGG GCCCAAGCTG CTCTCCAGCT | 1140 |
| AAATCACTAC CCGGTTTGTC CTGAACCGGA CCGAGCCATG GGTCTAGCAG CTCATACCGA | 1200 |
| CTCCACCCTC CTAACCATTC TGTACCAGAA CAATACCGCC GGTCTACAAG TATTTCGCGA | 1260 |
| TGATCTTGGT TGGGTCACCG TGCCACCGTT TCCTGGCTCG CTCGTGGTTA ACGTTGGTGA | 1320 |
| CCTCTTCCAC ATCCTATCCA ATGGATTGTT TAAAAGCGTG TTGCACCGCG CTCGGGTTAA | 1380 |
| CCAAACCAGA GCCCGGTTAT CTGTAGCATT CCTTTGGGGT CCGCAATCTG ATATCAAGAT | 1440 |
| ATCACCTGTA CCGAAGCTGG TTAGTCCCGT TGAATCGCCT CTATACCAAT CGGTGACATG | 1500 |
| GAAAGAGTAT CTTCGAACAA AGCAACTCA CTTCAACAAA GCTCTTTCAA TGATTAGAAA | 1560 |
| TCACAGAGAA GAATGATTAG ATAATAATAG TTGTGATCTA CTAGTTAGTT TGATTAATAA | 1620 |
| ATTGTTGTAA ATGATTTCAG CAATATGATT TGTTTGTCCT CAA | 1663 |

(2) INFORMATION FOR SEQ ID NO:4:

(i) SEQUENCE CHARACTERISTICS:
        (A) LENGTH: 377 amino acids (B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:4:

```
Met Ala Pro Val Ser Asn Glu Thr Phe Leu Pro Thr Glu Ala Trp Gly
1               5                   10                  15

Glu Ala Thr Leu Arg Pro Ser Phe Val Arg Asp Glu Asp Glu Arg Pro
            20                  25                  30

Lys Val Ala His Asp Arg Phe Ser Asp Ala Val Pro Leu Ile Ser Leu
        35                  40                  45

His Gly Ile Asp Gly Ala Arg Arg Ala Gln Ile Arg Asp Arg Val Ala
    50                  55                  60

Ala Ala Cys Glu Asp Trp Gly Ile Phe Gln Val Ile Asp His Gly Val
65                  70                  75                  80

Asp Ala Asp Leu Ile Ala Asp Met Thr Arg Leu Ala Arg Glu Phe Phe
                85                  90                  95

Ala Leu Pro Ala Glu Asp Lys Leu Arg Tyr Asp Met Ser Gly Gly Lys
            100                 105                 110

Lys Gly Gly Phe Ile Val Ser Ser His Leu Gln Gly Glu Ala Val Gln
        115                 120                 125

Asp Trp Arg Glu Ile Val Thr Tyr Phe Ser Tyr Pro Val Lys Ala Arg
    130                 135                 140

Asp Tyr Gly Arg Trp Pro Glu Lys Pro Ala Gly Trp Cys Ala Val Val
145                 150                 155                 160

Glu Arg Tyr Ser Glu Arg Leu Met Gly Leu Ser Cys Asn Leu Met Gly
                165                 170                 175

Val Leu Ser Glu Ala Met Gly Leu Glu Thr Glu Ala Leu Ala Lys Ala
            180                 185                 190

Cys Val Asp Met Asp Gln Lys Val Val Asn Phe Tyr Pro Arg Cys
    195                 200                 205

Pro Gln Pro Asp Leu Thr Leu Gly Leu Lys Arg His Thr Asp Pro Gly
    210                 215                 220

Thr Ile Thr Leu Leu Leu Gln Asp Leu Val Gly Gly Leu Gln Ala Thr
225                 230                 235                 240

Arg Asp Gly Gly Lys Asn Trp Ile Thr Val Gln Pro Ile Ser Gly Ala
                245                 250                 255

Phe Val Val Asn Leu Gly Asp His Gly His Phe Met Ser Asn Gly Arg
            260                 265                 270

Phe Lys Asn Ala Asp His Gln Ala Val Val Asn Gly Glu Ser Ser Arg
        275                 280                 285

Leu Ser Ile Ala Thr Phe Gln Asn Pro Ala Pro Asp Ala Arg Val Trp
    290                 295                 300

Pro Leu Ala Val Arg Glu Gly Glu Glu Pro Ile Leu Glu Glu Pro Ile
305                 310                 315                 320

Thr Phe Thr Glu Met Tyr Arg Arg Lys Met Glu Arg Asp Leu Asp Leu
                325                 330                 335

Ala Lys Arg Lys Lys Gln Ala Lys Asp Gln Leu Met Gln Gln Leu
        340                 345                 350

Gln Leu Gln Gln Gln Gln Ala Val Ala Ala Ala Pro Met Pro Thr Ala
        355                 360                 365

Thr Lys Pro Leu Asn Glu Ile Leu Ala
370                 375
```